(12) United States Patent
Hirohara et al.

(10) Patent No.: US 7,192,906 B2
(45) Date of Patent: Mar. 20, 2007

(54) SUBSTITUTED PYRAZOLE DERIVATIVES, PRODUCTION PROCESS THEREOF, AND HERBICIDE COMPOSITIONS CONTAINING THE DERIVATIVES

(75) Inventors: Yoji Hirohara, Ibaraki (JP); Eiji Ikuta, Ibaraki (JP); Sayo Osanai, Ibaraki (JP); Hideki Nakashima, Ibaraki (JP); Teruhiko Ishii, Ibaraki (JP)

(73) Assignee: SDS Biotech K.K., Tokyo (JP)

( * ) Notice: Subject to any disclaimer, the term of this patent is extended or adjusted under 35 U.S.C. 154(b) by 381 days.

(21) Appl. No.: 10/499,046

(22) PCT Filed: Dec. 18, 2002

(86) PCT No.: PCT/JP02/13245

§ 371 (c)(1),
(2), (4) Date: Jun. 16, 2004

(87) PCT Pub. No.: WO03/053937

PCT Pub. Date: Jul. 3, 2003

(65) Prior Publication Data

US 2005/0014649 A1    Jan. 20, 2005

(30) Foreign Application Priority Data

Dec. 20, 2001  (JP) ............... 2001-387578

(51) Int. Cl.
*A01N 43/56* (2006.01)
*C07D 231/10* (2006.01)

(52) U.S. Cl. ............... 504/280; 548/356.1; 548/373.1; 548/375.1; 504/209; 504/261

(58) Field of Classification Search ............ 548/356.1, 548/373.1, 375.1; 504/209, 261, 280
See application file for complete search history.

(56) References Cited

U.S. PATENT DOCUMENTS 4,066,776 A * 1/1978 Jones et al. ............... 514/363
4,072,498 A * 2/1978 Moon et al. ............... 504/249
6,809,065 B2 * 10/2004 Hirohara et al. ............ 504/156

FOREIGN PATENT DOCUMENTS

| EP | 0 288 789 A1 | 11/1988 |
| EP | 0 945 437 A1 | 9/1999 |
| JP | 10-130106 A | 5/1998 |
| JP | 10-158107 A | 6/1998 |

OTHER PUBLICATIONS

Gilchrist, Thomas L. et al., "Reaction of Azoles with Ethyl Bromopyruvate Oxime: Alkylation by Substitution and by Elimination—Addition", *Journal of Chemical Society Perkin Transaction 1*, 10, pp. 2235-2239 (1987).
Farm Chemicals Handbook '97, vol. 83, 1997 (2 pp.).
Shibuya Index (Index of Pesticides), 8th Ed., 1999, Shibuya Index Research Group (2 pp.).
The Pesticide Manual, 12th Ed., ® 2000, Editor: C D S Tomlin, British Crop Protection Council, Surrey UK (3 pp.).
Herbicide Research Conspectus, 1982, pub. Hakuyu-sha (2 pp.) (no English translation available).

* cited by examiner

Primary Examiner—Golam M. M. Shameem
(74) Attorney, Agent, or Firm—The Webb Law Firm

(57) ABSTRACT

Substituted pyrazole compounds of the formula (1). The compounds are synthesized from a pyrazole derivative and a haloalkyleneoxime ester derivative, and have excellent herbicidal effects. Herbicide compositions containing the substituted pyrazole derivatives or hydrazide derivatives thereof as active ingredients possess wide herbicidal spectra, work sufficiently in small dosages, and are sufficiently safe for certain important crops

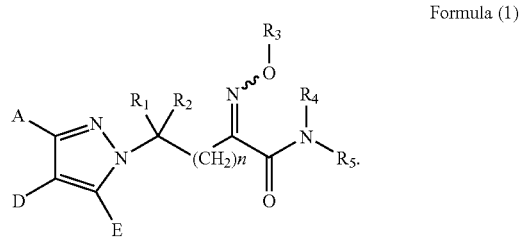

Formula (1)

5 Claims, No Drawings

SUBSTITUTED PYRAZOLE DERIVATIVES, PRODUCTION PROCESS THEREOF, AND HERBICIDE COMPOSITIONS CONTAINING THE DERIVATIVES

BACKGROUND OF THE INVENTION

1. Field of the Invention

The present invention relates to novel substituted pyrazole derivatives, production process thereof, and herbicide compositions containing the derivative(s) as active ingredient(s). More particularly, the invention relates to substituted pyrazole derivatives useful as herbicides, production process thereof, and herbicide compositions containing the derivative(s) as active ingredient(s). These are advantageous in the chemical industry and agriculture, particularly in the field of production of agricultural chemicals.

2. Description of the Prior Art

Herbicides developed so far and used are numerous. However, there are many species of weeds to be controlled, and emergence of the weeds lasts over a long period of time. Therefore, none of the many herbicide products can satisfy all the requirements in terms of, for example, herbicidal activity, herbicidal spectrum, crop selectivity, harmlessness to humans and environmental loads.

In cultivation of particularly important crops such as wheat, corn, soybeans and rice, a herbicide is desired that has effective herbicidal activity even in a small dose, broad herbicidal spectrum, sufficient residual effectiveness and excellent crop selectivity.

Attempts to search for pyrazoles having herbicidal activity for application in herbicides have been unsuccessful. The present applicant has disclosed substituted pyrazole derivatives as fungicides and synthesis processes thereof in Patent documents: JP-A-H10-130106; JP-A-H10-158107; and EP 00 945 437 A1. However, these documents do not provide any description as to herbicidal activity of the derivatives.

SUMMARY OF THE INVENTION

The present inventors synthesized novel substituted pyrazole derivatives represented by the following formula (1) and made various studies thereof. As a result, the inventors have determined that the derivatives have excellent herbicidal effects on a wide range of weeds including uncontrollable weeds and show sufficient harmlessness to a number of important crops. Based on the findings, the present invention has been accomplished.

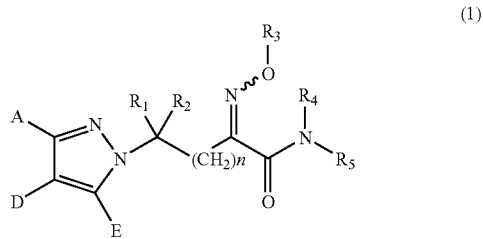

(1)

It is an object of the present invention to provide novel compounds that are harmless to crops and have high herbicidal effects. The invention has an object of providing novel substituted pyrazole derivatives of the following formula (1) (hereinafter "inventive compounds") and herbicide. compositions containing the derivative(s) as active ingredient(s).

The summary of the present invention is as follows.
The inventive compound is a substituted pyrazole derivative represented by the formula (1):

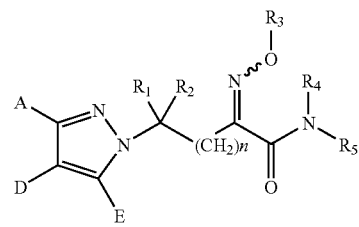

(1)

wherein:

n is 0 or 1; independently a group A is a hydrogen atom, a branched or unbranched alkyl group of 1 to 4 carbon atoms, a branched or unbranched haloalkyl group of 1 to 4 carbon atoms, a cycloalkyl group of 3 to 6 carbon atoms, or a phenyl group optionally having substituent groups;

said substituent groups being the same as or different from one another and selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, hydroxyl group, branched or unbranched haloalkoxy groups of 1 to 4 carbon atoms, branched or unbranched alkylcarbonyloxy groups of 1 to 4 carbon atoms, cycloalkylcarbonyloxy groups of 3 to 6 carbon atoms, branched or unbranched alkoxycarbonyloxy groups of 1 to 4 carbon atoms, branched or unbranched dialkylaminocarbonyloxy groups of 1 to 4 carbon atoms, branched or unbranched dialkylaminosulfonyloxy groups of 1 to 4 carbon atoms, branched or unbranched alkylthio groups of 1 to 4 carbon atoms, branched or unbranched haloalkylthio groups of 1 to 4 carbon atoms, branched or unbranched alkylsulfinyl groups of 1 to 4 carbon atoms, branched or unbranched haloalkylsulfinyl groups of 1 to 4 carbon atoms, branched or unbranched alkylsulfonyl groups of 1 to 4 carbon atoms, branched or unbranched haloalkylsulfonyl groups of 1 to 4 carbon atoms, halogen atoms, cyano group, nitro group, phenyl group optionally having substituent groups (the substituent groups are the same as the above substituent groups), phenoxy group optionally having substituent groups on the benzene ring (the substituent groups are the same as the above substituent groups) and benzyloxy group optionally having substituent groups on the benzene ring (the substituent groups are the same as the above substituent groups);

or said substituent groups being a group represented by the formula (2):

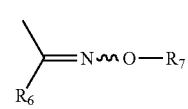

(2)

wherein $R_6$ and $R_7$ are the same or different and each denotes a hydrogen atom or a branched or unbranched alkyl group of 1 to 4 carbon atoms;

or said substituent groups being a group represented by the formula (3):

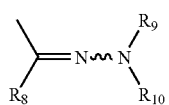
(3)

wherein $R_8$, $R_9$ and $R_{10}$ are the same or different and each denotes a hydrogen atom or a branched or unbranched alkyl group of 1 to 4 carbon atoms;

said substituent groups substituting a hydrogen atom at 0 to 5 arbitrary positions of the phenyl group;

a group D is a hydrogen atom, a branched or unbranched alkyl group of 1 to 4 carbon atoms, a branched or unbranched haloalkyl group of 1 to 4 carbon atoms, an alkenyl group of 2 to 4 carbon atoms, an alkynyl group of 2 to 4 carbon atoms, a branched or unbranched alkoxy group of 1 to 4 carbon atoms, a cycloalkyl group of 3 to 6 carbon atoms, a cyano group, a halogen atom, a branched or unbranched alkoxycarbonyl group of 1 to 4 carbon atoms, a branched or unbranched alkylthio group of 1 to 4 carbon atoms, a branched or unbranched alkylsulfinyl group of 1 to 4 carbon atoms, a branched or unbranched alkylsulfonyl group of 1 to 4 carbon atoms, or a phenyl group optionally having substituent groups (the substituent groups are the same as the aforesaid substituent groups), said substituent groups substituting a hydrogen atom at 0 to 5 arbitrary positions of the phenyl group;

a group E is a hydrogen atom, a branched or unbranched alkyl group of 1 to 4 carbon atoms, a cycloalkyl group of 3 to 6 carbon atoms, a halogen atom, or a phenyl group optionally having substituent groups (the substituent groups are the same as the aforesaid substituent groups), said substituent groups substituting a hydrogen atom at 0 to 5 arbitrary positions of the phenyl group;

groups $R_1$ and $R_2$ are the same or different and each denotes a hydrogen atom, a halogen atom, a branched or unbranched alkyl group of 1 to 4 carbon atoms, or a branched or unbranched haloalkyl group of 1 to 4 carbon atoms;

a group $R_3$ is a hydrogen atom, a branched or unbranched alkyl group of 1 to 4 carbon atoms, a branched or unbranched haloalkyl group of 1 to 4 carbon atoms, an alkenyl group of 2 to 4 carbon atoms, an alkynyl group of 2 to 4 carbon atoms, or a branched or unbranched alkoxyalkyl group of 1 to 4 carbon atoms;

groups $R_4$ and $R_5$ are the same or different and each denotes a hydrogen atom, a branched or unbranched alkyl group of 1 to 4 carbon atoms, a branched or unbranched haloalkyl group of 1 to 4 carbon atoms, a cycloalkyl group of 3 to 8 carbon atoms which may be substituted with a branched or unbranched alkyl group of 1 to 4 carbon atoms, an alkenyl group of 2 to 4 carbon atoms, an alkynyl group of 2 to 4 carbon atoms, a branched or unbranched alkoxyalkyl group of 1 to 4 carbon atoms, a cyanomethyl group, a substituted or unsubstituted amino group, or a phenyl group optionally having substituent groups;

said substituent groups being the same as or different from one another and selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group, wherein said substituent groups substitute a hydrogen atom at 0 to 5 arbitrary positions of the phenyl group;

or groups $R_4$ and $R_5$ are each a benzyl group optionally having substituent groups on the benzene ring;

said substituent groups being the same as or different from one another and selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group, wherein said substituent groups substitute a hydrogen atom at 0 to 5 arbitrary positions of the benzene ring;

or groups $R_4$ and $R_5$ are each an α- or β-phenethyl group optionally having substituent groups on the benzene ring, said substituent groups being selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group, wherein said substituent groups substitute a hydrogen atom at 0 to 5 arbitrary positions of the benzene ring;

or groups $R_4$ and $R_5$ together form a five-membered or six-membered aliphatic ring, wherein said ring may be substituted with a group selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group, and said ring may contain one or two heteroatoms.

A substituted pyrazole hydrazide derivative according to the present invention has the above formula (1) in which $R_4$ is a hydrogen atom and $R_5$ is a substituted amino group —N($R_{11}$,$R_{12}$), and is represented by the following formula (4):

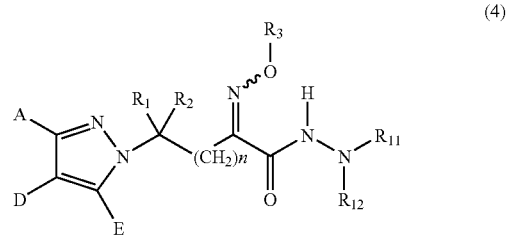
(4)

wherein:

n is 0 or 1;

each group A, D, E, $R_1$, $R_2$ and $R_3$ denotes independently the same substituent groups as in the formula (1); and groups $R_{11}$ and $R_{12}$ are the same or different and each denotes a hydrogen atom, a branched or unbranched alkyl group of 1 to 4 carbon atoms, a branched or unbranched haloalkyl group of 1 to 4 carbon atoms, a branched or unbranched alkoxycarbonyl group of 1 to 4 carbon atoms, or a phenyl group optionally having substituent groups, said substituent groups being the same as or different from one another and selected from alkyl groups of 1 to 4 carbon atoms, haloalkyl groups of 1 to 4 carbon atoms, alkoxy groups of 1 to 4 carbon atoms, haloalkoxy groups of 1 to 4 carbon atoms (these groups may be branched or unbranched), halogen atoms, cyano group and nitro group, wherein said substituent groups substitute a hydrogen atom at 0 to 5 arbitrary positions of the phenyl group.

A process for preparing substituted pyrazole derivatives of the formula (1) comprises reacting a pyrazole derivative of the formula (5) with a haloalkyleneoxime ester derivative of the formula (6) to obtain a pyrazole derivative ester of the formula (7):

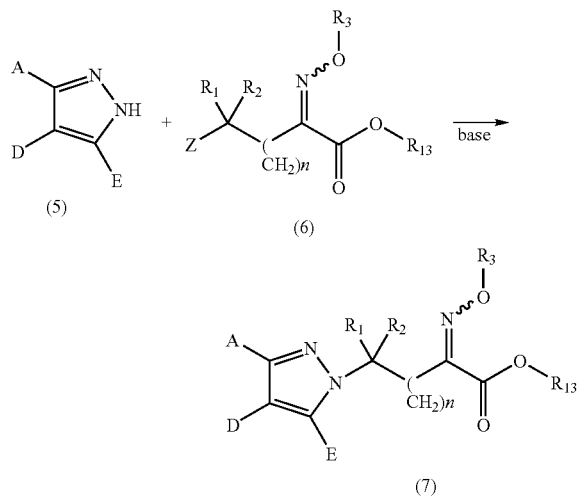

and hydrolyzing the ester group of the pyrazole derivative ester of the formula (7) in the presence of a base to yield a carboxylic acid derivative of the formula (8) and reacting the carboxylic acid derivative with an amine $R_4$—NH—$R_5$ in the presence of a condensation agent:

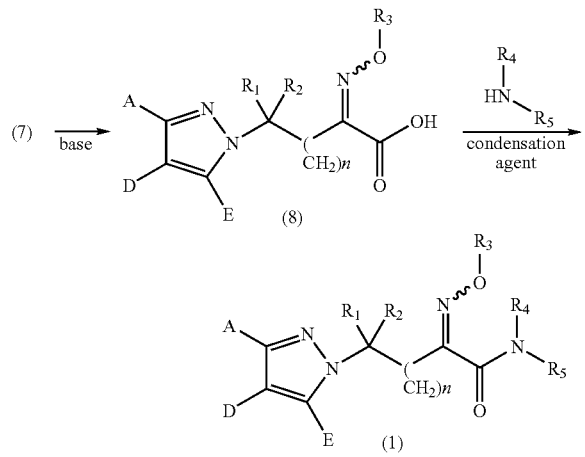

wherein in the formulae (5) to (8), n is 0 or 1, a group Z is a halogen atom, a group $R_{13}$ is a methyl or ethyl group, and each group A, D, E, $R_1$, $R_2$, $R_3$, $R_4$ and $R_5$ denotes independently the same substituent groups as in the formula (1).

A process for preparing the haloalkyleneoxime ester derivative of the formula (6) according to the present invention comprises allowing a hydroxylamine derivative of the formula (19) to act on a halopyruvate derivative of the formula (18) in the presence of a solvent, said hydroxylamine derivative being used in 1 or more equivalents per equivalent of said halopyruvate derivative:

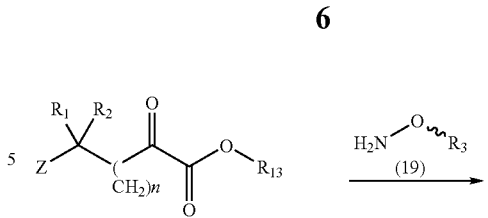

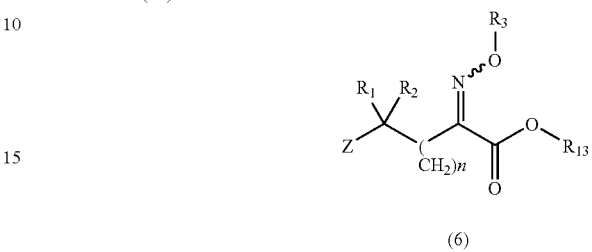

wherein n is 0 or 1, a group Z is a halogen atom, a group $R_{13}$ is a methyl or ethyl group, and each group $R_1$, $R_2$ and $R_3$ denotes independently the same substituent groups as in the formula (1).

A herbicide composition according to the present invention comprises one or more kinds of the substituted pyrazole derivatives of the formula (1) as active ingredients.

A herbicide composition according to the present invention comprises one or more kinds of the substituted pyrazole derivatives of the formula (4) as active ingredients.

The inventive compound is a substituted pyrazole derivative preferably represented by the following formula (1):

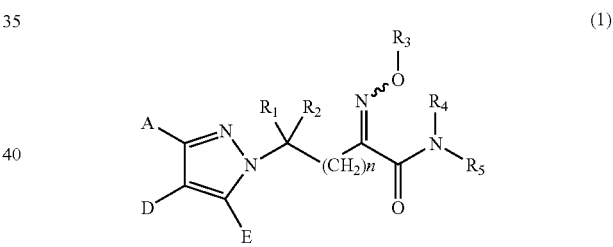

wherein:
n is 0 or 1; independently a group A is a hydrogen atom, a branched or unbranched alkyl group of 1 to 4 carbon atoms, a branched or unbranched haloalkyl group of 1 to 4 carbon atoms, a cycloalkyl group of 3 to 6 carbon atoms, or a phenyl group substituted with 0 to 5 substituent groups (0 substituent group means an unsubstituted phenyl group);

said substituent groups being the same as or different from one another and selected from alkyl groups of 1 to 4 carbon atoms, haloalkyl groups of 1 to 4 carbon atoms, alkoxy groups of 1 to 4 carbon atoms, haloalkoxy groups of 1 to 4 carbon atoms, alkylcarbonyloxy groups of 1 to 4 carbon atoms, alkoxycarbonyloxy groups of 1 to 4 carbon atoms, dialkylaminocarbonyloxy groups of 1 to 4 carbon atoms, alkylthio groups of 1 to 4 carbon atoms, haloalkylthio groups of 1 to 4 carbon atoms, alkylsulfinyl groups of 1 to 4 carbon atoms, haloalkylsulfinyl groups of 1 to 4 carbon atoms (these groups may be linear or branched), halogen atoms, hydroxyl group, cyano group, N-hydroxyimino group, N-methoxyimino group, N,N-dimethylaminoimino group, phenyl group, phenoxy group and benzyloxy group;

a group D is a hydrogen atom, a halogen atom, a branched or unbranched alkyl group of 1 to 4 carbon atoms, a branched or unbranched haloalkyl group of 1 to 4 carbon atoms, an alkynyl group of 2 to 4 carbon atoms, a branched or unbranched alkoxy group of 1 to 4 carbon atoms, an alkoxycarbonyl group of 1 to 4 carbon atoms, an alkylsulfinyl group of 1 to 4 carbon atoms or a phenyl group;

a group E is a hydrogen atom, a halogen atom, a branched or unbranched alkyl group of 1 to 4 carbon atoms or a phenyl group;

groups $R_1$ and $R_2$ are each a hydrogen atom or a methyl group;

a group $R_3$ is a hydrogen atom, a branched or unbranched alkyl group of 1 to 4 carbon atoms, an alkenyl group of 2 to 4 carbon atoms, an alkynyl group of 2 to 4 carbon atoms, a branched or unbranched alkoxyalkyl group of 1 to 4 carbon atoms, a fluoromethyl group or a benzyl group;

groups $R_4$ and $R_5$ together form a five-membered or six-membered aliphatic ring which may contain 1 or 2 heteroatoms and which may be substituted with an alkyl group of 1 to 4 carbon atoms, or independently a group $R_4$ is a hydrogen atom or a branched or unbranched alkyl group of 1 to 4 carbon atoms, and a group $R_5$ is a hydrogen atom, a branched or unbranched alkyl group of 1 to 4 carbon atoms, a branched or unbranched haloalkyl group of 1 to 4 carbon atoms, a branched or unbranched cyanoalkyl group of 1 to 4 carbon atoms, a cycloalkyl group of 3 to 6 carbon atoms which may be substituted with a branched or unbranched alkyl group of 1 to 4 carbon atoms, an alkenyl group of 2 to 4 carbon atoms, an alkynyl group of 2 to 4 carbon atoms, a phenyl group, a benzyl group, or an α- or β-phenethyl group optionally having a (branched or unbranched) alkoxy group of 1 to 4 carbon atoms on the benzene ring.

The inventive compound is a substituted pyrazole derivative having the formula (1) in which $R_4$ is a hydrogen atom and $R_5$ is a substituted amino group $-N(R_{11}, R_{12})$, and is represented by the following formula (4):

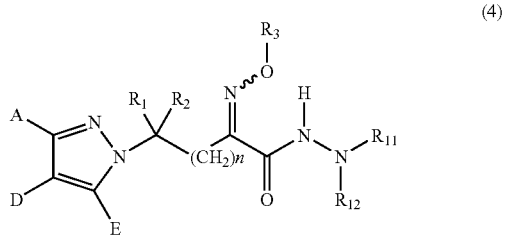

(4)

wherein:

n is 0 or 1;

each group A, D, E, $R_1$, $R_2$ and $R_3$ denotes independently the same substituent groups as in the formula (1); and groups $R_{11}$ and $R_{12}$ are the same or different and each denotes a hydrogen atom, an alkyl group of 1 to 4 carbon atoms, a haloalkyl group of 1 to 4 carbon atoms or an alkoxycarbonyl group of 1 to 4 carbon atoms (these groups may be branched or unbranched).

A herbicide composition according to the present invention comprises one or more kinds of the above substituted pyrazoles preferably as active ingredients.

A herbicide composition according to the present invention comprises one or more kinds of the substituted pyrazole hydrazide derivatives as active ingredients.

DETAILED DESCRIPTION OF THE INVENTION

The substituted pyrazole derivatives (also referred to as "inventive compounds") are novel compounds showing sufficient harmlessness to important crops, while exhibiting excellent herbicidal activity, and possess a structure represented by the formula (1) or (4). The inventive compounds have a common skeleton composed of a substituted pyrazole ring and an N-oxime acid amide. The substituted pyrazole derivative of the formula (4) is a hydrazide derivative of the compound of the formula (1). The inventive compounds are illustrated hereinbelow as ones having specific groups, but are not limited thereto.

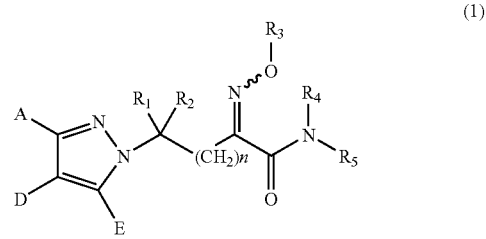

(1)

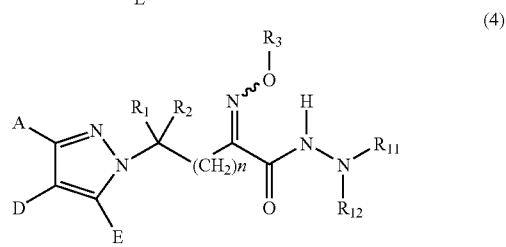

(4)

The scope of the present invention includes derivatives of the inventive compounds having various substituent groups, salts (e.g., sodium salts, potassium salts, magnesium salts, calcium salts, aluminum salts, zinc salts), hydrates, solvates and crystal polymorphs of the compounds. Further, stereoisomers are possible when the inventive compounds contain an asymmetric carbon (for example, when $R_1$ and $R_2$ in the formula (1) or (4) are different each other). The inventive compounds encompass all the possible isomers and mixtures containing two or more isomers in arbitrary proportions.

Hereinbelow, detailed structures of the inventive compounds (1) and (4), production processes, herbicidal effects, formulations and application methods thereof will be described in the order named.

Substituted Pyrazole Derivatives

The inventive compounds are substituted pyrazole derivatives comprising a substituted pyrazole ring and an N-oxime acid amide as illustrated in the formula (1), and hydrazide derivatives thereof (represented by the formula (4)) In the formulae (1) and (4), n is 0 or 1. In either case, the acid amides (1) and hydrazide derivatives thereof (4) of the present invention may contain a hydrogen atom and other groups described below as substituent groups A, D, E, $R_1$ to $R_5$, $R_{11}$ and $R_{12}$.

The group A in the formula (1) is a hydrogen atom, a branched or unbranched alkyl group of 1 to 4 carbon atoms, a branched or unbranched haloalkyl group of 1 to 4 carbon atoms, a cycloalkyl group of 3 to 6 carbon atoms, or a phenyl group optionally having one or more substituent groups listed below.

The substituent groups of the phenyl group may be the same as or different from one another and be selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, branched or unbranched alkylcarbonyloxy groups of 1 to 4 carbon atoms, cycloalkylcarbonyloxy groups of 3 to 6 carbon atoms, branched or unbranched alkoxycarbonyloxy groups of 1 to 4 carbon atoms, branched or unbranched dialkylaminocarbonyloxy groups of 1 to 4 carbon atoms, branched or unbranched dialkylaminosulfonyloxy groups of 1 to 4 carbon atoms, branched or unbranched alkylthio groups of 1 to 4 carbon atoms, branched or unbranched haloalkylthio groups of 1 to 4 carbon atoms, branched or unbranched alkylsulfinyl groups of 1 to 4 carbon atoms, branched or unbranched haloalkylsulfinyl groups of 1 to 4 carbon atoms, branched or unbranched alkylsulfonyl groups of 1 to 4 carbon atoms, branched or unbranched haloalkylsulfonyl groups of 1 to 4 carbon atoms, halogen atoms, hydroxyl group, cyano group, nitro group, phenyl group optionally having one or more substituent groups (these substituent groups are the same as the aforesaid substituent groups), phenoxy group optionally having one or more substituent groups on the benzene ring (these substituent groups are the same as the aforesaid substituent groups) and benzyloxy group optionally having one or more substituent groups on the benzene ring (these substituent groups are the same as the aforesaid substituent groups).

The aforesaid substituent groups of the phenyl group may be otherwise a group represented by the formula (2):

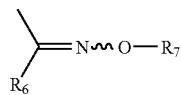
(2)

wherein $R_6$ and $R_7$ are the same or different and each denotes a hydrogen atom or a branched or unbranched alkyl group of 1 to 4 carbon atoms.

Alternatively, the substituent groups of the phenyl group may be a group having the formula (3):

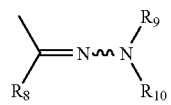
(3)

wherein $R_8$, $R_9$ and $R_{10}$ are the same or different and each denotes a hydrogen atom or a branched or unbranched alkyl group of 1 to 4 carbon atoms.

These exemplified substituent groups may substitute a hydrogen atom at 0 to 5 arbitrary positions of the phenyl group.

Specific examples of the above-mentioned groups are listed below without limiting the scope of the invention.

The branched or unbranched alkyl groups of 1 to 4 carbon atoms include methyl, ethyl, propyl and butyl groups, and isomer groups thereof.

The branched or unbranched haloalkyl groups of 1 to 4 carbon atoms include fluoromethyl, difluoromethyl, trifluoromethyl, dichloroethyl and bromopropyl groups, and isomer groups thereof.

The cycloalkyl groups of 3 to 6 carbon atoms include cyclopropyl, cyclobutyl, cyclopentyl and cyclohexyl groups.

The "phenyl group optionally having one or more substituent groups" given as an exemplary group A in the formula (1) refers to a phenyl group substituted with same or different substituent group(s) at 0 to 5 arbitrary positions. Examples of the substituent groups include branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, branched or unbranched alkylcarbonyloxy groups of 1 to 4 carbon atoms, cycloalkylcarbonyloxy groups of 3 to 6 carbon atoms, branched or unbranched alkoxycarbonyloxy groups of 1 to 4 carbon atoms, branched or unbranched dialkylaminocarbonyloxy groups of 1 to 4 carbon atoms, branched or unbranched dialkylaminosulfonyloxy groups of 1 to 4 carbon atoms, branched or unbranched alkylthio groups of 1 to 4 carbon atoms, branched or unbranched haloalkylthio groups of 1 to 4 carbon atoms, branched or unbranched alkylsulfinyl groups of 1 to 4 carbon atoms, branched or unbranched haloalkylsulfinyl groups of 1 to 4 carbon atoms, branched or unbranched alkylsulfonyl groups of 1 to 4 carbon atoms, branched or unbranched haloalkylsulfonyl groups of 1 to 4 carbon atoms halogen atoms, hydroxyl group, cyano group and nitro group. Specific examples of the alkyl groups and haloalkyl groups include, but not limited to, the groups described hereinabove.

The branched or unbranched alkoxy groups of 1 to 4 carbon atoms include methoxy, ethoxy, propoxy and butoxy groups, and isomer groups thereof.

The branched or unbranched haloalkoxy groups of 1 to 4 carbon atoms include monofluoromethoxy and chloropropoxy groups, and isomer groups thereof.

The branched or unbranched alkylcarbonyloxy groups of 1 to 4 carbon atoms include methylcarbonyloxy, ethylcarbonyloxy, propylcarbonyloxy and butylcarbonyloxy groups.

The cycloalkylcarbonyloxy groups of 3 to 6 carbon atoms include cyclopentylcarbonyloxy and cyclohexylcarbonyloxy groups.

The branched or unbranched alkoxycarbonyloxy groups of 1 to 4 carbon atoms include methoxycarbonyloxy, ethoxycarbonyloxy, propoxycarbonyloxy and butoxycarbonyloxy groups.

The branched or unbranched dialkylaminocarbonyloxy groups of 1 to 4 carbon atoms include dimethylaminocarbonyloxy and diethylaminocarbonyloxy groups.

The branched or unbranched dialkylaminosulfonyloxy groups of 1 to 4 carbon atoms include dimethylaminosulfonyloxy and diethylaminosulfonyloxy groups.

The branched or unbranched alkylthio groups of 1 to 4 carbon atoms include methylthio, ethylthio, propylthio and butylthio groups, and isomer groups thereof.

The branched or unbranched haloalkylthio groups of 1 to 4 carbon groups include monochloromethylthio and trifluoromethylthio groups.

The branched or unbranched alkylsulfinyl groups of 1 to 4 carbon atoms include methylsulfinyl, ethylsulfinyl, propylsulfinyl and butylsulfinyl groups, and isomer groups thereof.

The branched or unbranched haloalkylsulfinyl groups of 1 to 4 carbon atoms include monochloromethylsulfinyl and monofluoromethylsulfinyl groups.

The branched or unbranched alkylsulfonyl groups of 1 to 4 carbon atoms include methylsulfonyl, ethylsulfonyl, propylsulfonyl and butylsulfonyl groups, and isomer groups thereof.

The branched or unbranched haloalkylsulfonyl groups of 1 to 4 carbon atoms include monobromomethylsulfonyl and monofluoromethylsulfonyl groups.

The halogen atoms include fluorine, chlorine, bromine and iodine atoms.

The arbitrary substituent groups on the phenyl group may each be a phenyl group optionally having further one or more substituent groups (these substituent groups are the same as the aforesaid substituent groups), a phenoxy group optionally having one or more substituent groups on the benzene ring (these substituent groups are the same as the aforesaid substituent groups), or a benzyloxy group optionally having one or more substituent groups on the benzene ring (these substituent groups are the same as the aforesaid substituent groups). Specific examples of such substituted phenyl groups (having one or more substituent groups on the benzene ring) include methylphenyl group, chlorophenyl group, dichlorophenyl group, 3(1-(chlorobenzyloxyimino)-ethyl)phenyl group, 3-(benzyloxy)phenyl group, 3-(methylbenzyloxy)phenyl group, 3-(chlorobenzyloxy)phenyl group, 3-(cyanobenzyloxy)phenyl group, 3-(dimethylbenzyloxy)phenyl group, 3-(dichlorobenzyloxy)phenyl group, 3-(pyridylmethoxy)phenyl group, 3-(benzoyloxy)phenyl group, 3-(chlorobenzoyloxy)phenyl group, benzyl group, phenoxymethyl group, methylphenoxymethyl group, phenylthiomethyl group, methylphenylthiomethyl group, 1-phenoxyethyl group, 1-(methylphenoxy)ethyl group, 1-phenylthioethyl group, 1-(methylphenylthio)ethyl group, phenoxy group, 2-methylphenoxy group, 3-methylphenoxy group, 4-methylphenoxy group, 2-chlorophenoxy group, 3-chlorophenoxy group, 4-chlorophenoxy group, 2-trifluoromethylphenoxy group, 2,5-dimethylphenoxy group, 2,5-dichlorophenoxy group, 2-chloro-5-trifluoromethylphenoxy group, phenylthio group, 2-methylphenylthio group, benzyloxy group, 2-methylbenzyloxy group, 3-methylbenzyloxy group, 4-methylbenzyloxy group, 2-chlorobenzyloxy group, 3-chlorobenzyloxy group, 4-chlorobenzyloxy group, 2-trifluoromethylbenzyloxy group, 2,5-dimethylbenzyloxy group, 2,5-dichlorobenzyloxy group, 2-chloro-5-trifluoromethylbenzyloxy group, benzylthio group, 2-methylbenzylthio group, benzyloxyiminomethyl group, 2-methylbenzyloxyiminomethyl group, 3-methylbenzyloxyiminomethyl group and 4-methylbenzyloxyiminomethyl group.

Further, groups represented by the following formula (2) or (3) are also available as the arbitrary substituent groups on the phenyl group:

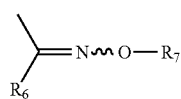

(2)

wherein $R_6$ and $R_7$ may be the same or different and each denotes a hydrogen atom or a branched or unbranched alkyl group of 1 to 4 carbon atoms;

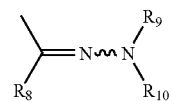

(3)

wherein $R_8$, $R_9$ and $R_{10}$ may be the same or different and each denotes a hydrogen atom or a branched or unbranched alkyl group of 1 to 4 carbon atoms.

The branched or unbranched alkyl groups of 1 to 4 carbon atoms for the above groups ($R_6$, $R_7$, $R_8$, $R_9$ and $R_{10}$) include the alkyl groups listed above, but are not limited thereto.

Of the groups A listed above, particularly preferred are a hydrogen atom, methyl group, ethyl group, n-propyl group, i-propyl group, n-butyl group, t-butyl group, trifluoromethyl group, cyclopropyl group, cyclobutyl group, cyclopentyl group, cyclohexyl group, phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2,3-difluorophenyl group, 2,4-difluorophenyl group, 2,5-difluorophenyl group, 2,6-difluorophenyl group, 3,4-difluorophenyl group, 3,5-difluorophenyl group, 2,5-dichlorophenyl group, 2-fluoro-4-chlorophenyl group, 3-fluoro-4-chlorophenyl group, 4-fluoro-2-chlorophenyl group, 4-fluoro-3-bromophenyl group, 4-cyanophenyl group, 2-methylphenyl group, 3-methylphenyl group, 4-methylphenyl group, 3,4-dimethylphenyl group, 3-fluoro-4-methylphenyl group, 4-fluoro-3-methylphenyl group, 2-fluoro-3-trifluoromethylphenyl group, 2-fluoro-4-trifluoromethylphenyl group, 2-fluoro-5-trifluoromethylphenyl group, 3-fluoro-4-trifluoromethylphenyl group, 3-fluoro-5-trifluoromethylphenyl group, 4-fluoro-2-trifluoromethylphenyl group, 4-fluoro-3-trifluoromethylphenyl group, 4-isopropylphenyl group, 4-trifluoromethylphenyl group, 4-hydroxyphenyl group, 4-acetyloxyphenyl group, dimethylaminocarbonyloxyphenyl group, dimethylaminosulfinyloxyphenyl group, 4-methylthiophenyl group, 4-methylsulfinylphenyl group, 4-trifluoromethylthiophenyl group, 4-methoxyphenyl group, 2,3-dimethoxyphenyl group, 3-fluoro-4-methoxyphenyl group, 4-fluoro-3-methoxyphenyl group, 2-chloro-4-methoxyphenyl group, 3-chloro-4-methoxyphenyl group, 4-difluoromethoxyphenyl group, 4-trifluoromethoxyphenyl group, 4-(2,1,1-trifluoroethoxy)phenyl group, 2-difluoromethoxy-4-methoxyphenyl group, 3,5-difluoro-4-methoxyphenyl group, 4-phenylphenyl group, 3-phenoxyphenyl group, 4-phenoxyphenyl group, 4-benzyloxyphenyl group, 4-(N-hydroxyimino)phenyl group, 4-(N-methoxyimino)phenyl group and 4-(N,N-dimethylaminoxyimino)phenyl group.

The group D in the formula (1) is a hydrogen atom, a branched or unbranched alkyl group of 1 to 4 carbon atoms, a branched or unbranched haloalkyl group of 1 to 4 carbon atoms, an alkenyl group of 2 to 4 carbon atoms, an alkynyl group of 2 to 4 carbon atoms, a branched or unbranched alkoxy group of 1 to 4 carbon atoms, a cycloalkyl group of 3 to 6 carbon atoms, a cyano group, a halogen atom, a branched or unbranched alkoxycarbonyl group of 1 to 4 carbon atoms, a branched or unbranched alkylthio group of 1 to 4 carbon atoms, a branched or unbranched alkylsulfinyl group of 1 to 4 carbon atoms, a branched or unbranched alkylsulfonyl group of 1 to 4 carbon atoms, or a phenyl group optionally having one or more substituent groups (these substituent groups are the same as the aforesaid substituent groups). The exemplified substituent groups may substitute a hydrogen atom at 0 to 5 arbitrary positions of the phenyl group.

The alkenyl groups of 2 to 4 carbon atoms include vinyl, propenyl and butenyl groups. For the latter two groups, isomer groups based on the double bond are possible.

The alkynyl groups of 2 to 4 carbon atoms include linear or branched ethynyl, propynyl and butynyl groups, and isomer groups thereof.

The branched or unbranched alkoxycarbonyl groups of 1 to 4 carbon atoms include methoxycarbonyl, ethoxycarbonyl and propoxycarbonyl groups.

Specific examples of the other groups as the group D include the aforesaid groups, but are not limited thereto.

Of the groups for D listed above, preferred are a hydrogen atom, chlorine atom, methyl group, ethyl group, ethynyl group, trifluoromethyl group, methylsulfinyl group, ethoxycarbonyl group and phenyl group.

The group E in the formula (1) is a hydrogen atom, a branched or unbranched alkyl group of 1 to 4 carbon atoms, a cycloalkyl group of 3 to 6 carbon atoms, a halogen atom, or a phenyl group optionally having one or more substituent groups (these substituent groups are the same as the aforesaid substituent groups). The exemplified substituent groups may substitute a hydrogen atom at 0 to 5 arbitrary positions of the phenyl group. Specific examples of these groups include those mentioned hereinabove, but are not limited thereto.

Of the groups for E listed above, preferred are a hydrogen atom, halogen atom, branched or unbranched alkyl group of 1 to 4 carbon atoms and phenyl group.

The groups $R_1$ and $R_2$ may be the same or different each other and each denotes a hydrogen atom, a halogen atom, a branched or unbranched alkyl group of 1 to 4 carbon atoms, or a branched or unbranched haloalkyl group of 1 to 4 carbon atoms. Specific examples of these groups include those mentioned hereinabove, but are not limited thereto. Of the groups listed as $R_1$ and $R_2$, preferred are a hydrogen atom and methyl group. Particularly preferably, the groups $R_1$ and $R_2$ are both hydrogen atoms.

The group $R_3$ is a hydrogen atom, a branched or unbranched alkyl group of 1 to 4 carbon atoms, a branched or unbranched haloalkyl group of 1 to 4 carbon atoms, an alkenyl group of 2 to 4 carbon atoms, an alkynyl group of 2 to 4 carbon atoms, or a branched or unbranched alkoxyalkyl group of 1 to 4 carbon atoms. Specific examples of these groups are as described hereinabove, but are not limited thereto. Of the groups for $R_3$, preferred are a hydrogen atom, branched or unbranched alkyl group of 1 to 4 carbon atoms, alkenyl group of 2 to 4 carbon atoms, alkynyl group of 2 to 4 carbon atoms, branched or unbranched alkoxyalkyl group of 1 to 4 carbon atoms, fluoromethyl group and benzyl group.

The groups $R_4$ and $R_5$ may be the same or different each other and each denotes a hydrogen atom, a branched or unbranched alkyl group of 1 to 4 carbon atoms, a branched or unbranched haloalkyl group of 1 to 4 carbon atoms, a cycloalkyl group of 3 to 8 carbon atoms which may be substituted with a branched or unbranched alkyl group of 1 to 4 carbon atoms, an alkenyl group of 2 to 4 carbon atoms, an alkynyl group of 2 to 4 carbon atoms, a branched or unbranched alkoxyalkyl group of 1 to 4 carbon atoms, a substituted or unsubstituted amino group, a cyanomethyl group, or a phenyl group substituted with 0 to 5 arbitrary substituent groups mentioned as hereunder. Such substituent groups may be the same as or different from one another and are selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group. The exemplified substituent groups may substitute a hydrogen atom at 0 to 5 arbitrary positions of the phenyl group.

Further, the groups $R_4$ and $R_5$ may each be a benzyl group optionally having one or more substituent groups on the benzene ring. The substituent groups may be the same as or different from one another and are selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group. The exemplified substituent groups may substitute a hydrogen atom at 0 to 5 arbitrary positions of the benzene ring of the benzyl group.

Furthermore, the groups $R_4$ and $R_5$ may each be an α- or β-phenethyl group optionally having one or more substituent groups on the benzene ring. The substituent groups are selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group. The exemplified substituent groups may substitute a hydrogen atom at 0 to 5 arbitrary positions of the benzene ring of the α- or β-phenethyl group.

Examples of the branched or unbranched alkyl groups of 1 to 4 carbon atoms, branched or unbranched haloalkyl groups of 1 to 4 carbon atoms, alkenyl groups of 2 to 4 carbon atoms, alkynyl groups of 2 to 4 carbon atoms, branched or unbranched alkoxyalkyl groups of 1 to 4 carbon atoms, branched or unbranched haloalkyl groups of 1 to 4 carbon atoms, halogen atoms and substituted phenyl groups include the groups described hereinabove, but are not limited thereto.

Examples of the substituted or unsubstituted amino group include amino group and substituted amino groups such as dimethylamino group, diethylamino group, dipropylamino group, dibutylamino group, ethylmethylamino group, diphenylamino group, anilino group, anisidino group, phenetidino group, toluidino group, xylidino group, methoxycarbonylamino group, cyclopropylamino group and ethynylamino group.

Examples of the cycloalkyl groups of 3 to 8 carbon atoms which may be substituted with a branched or unbranched alkyl group of 1 to 4 carbon atoms include cyclopropyl group, cyclobutyl group, cyclopentyl group, cyclohexyl group, cycloheptyl group, cyclooctyl group, and these alicyclic groups substituted with a branched or unbranched alkyl group of 1 to 4 carbon atoms.

Of the groups listed above for $R_4$, a hydrogen atom, methyl group and ethyl group are preferred. Of the groups listed above for $R_5$, preferred are a hydrogen atom, branched or unbranched alkyl group of 1 to 4 carbon atoms, branched or unbranched haloalkyl group of 1 to 4 carbon atoms, branched or unbranched cyanoalkyl group of 1 to 4 carbon atoms, cycloalkyl group of 3 to 6 carbon atoms which may be substituted with an alkyl group, substituted or unsubstituted phenyl group, substituted or unsubstituted benzyl group and substituted or unsubstituted phenethyl group.

Furthermore, the groups $R_4$ and $R_5$ may together form a five-membered or six-membered aliphatic ring. The ring may contain one or two heteroatoms. The heteroatoms in the aliphatic ring include nitrogen, oxygen, sulfur, phosphorous and arsenic. The five-membered or six-membered ring may be substituted with a group selected from alkyl groups of 1 to 4 carbon atoms, branched or unbranched haloalkyl groups of 1 to 4 carbon atoms, branched or unbranched alkoxy groups of 1 to 4 carbon atoms, haloalkoxy groups of 1 to 4 carbon atoms, halogen atoms, cyano group and nitro group.

In a particularly preferable embodiment of the inventive compounds, $R_4$ and $R_5$ together form a heteroalicyclic group such as a five-membered or six-membered ring containing one nitrogen atom, or a six-membered ring containing one nitrogen atom and one oxygen or sulfur atom (e.g., Compounds Nos. 118–122 in Table 1 of Examples presented later).

Specific examples of the group —$N(R_4R_5)$ in the formula (1) are given below, including the cases where $R_4$ and $R_5$ together form a five-membered or six-membered aliphatic ring substituted with an alkyl group of 1 to 4 carbon atoms or the like. In the formulae given below, Me, Et, Pr, Bu, i, t, pen and hex denote methyl, ethyl, propyl, butyl, iso, tertiary, pentyl and hexyl, respectively.

—NHMe, —NHEt, —NH-i-Pr, —NH-c-Pr, —NH-t-Bu, —NH-c-pen,

—NH-c-hex

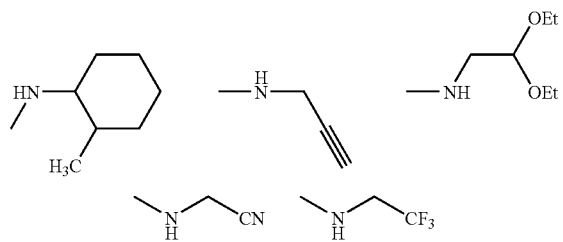

Aliphatic primary amines

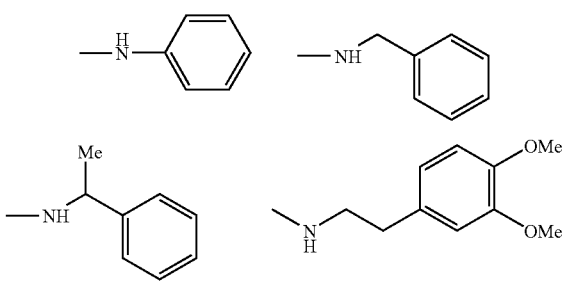

Aromatic primary amines

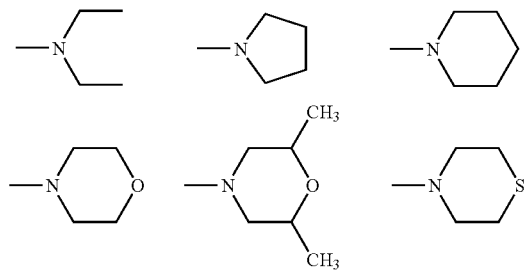

Aliphatic secondary amines

-continued

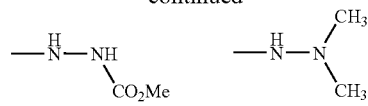

Hydrazides

Table 1 lists Compounds Nos. 1 to 124 synthesized in Examples (described later) as typical examples of the substituted pyrazole derivatives of the formula (1) according to the present invention. However, the inventive compounds are not limited thereto.

When $R_4$ is a hydrogen atom and $R_5$ is a substituted amino group —$N(R_{11},R_{12})$ in reference to the formula (1), in particular, the inventive compound is a substituted pyrazole hydrazide derivative represented by the formula (4):

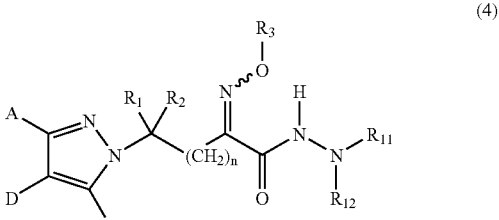

wherein:

n is 0 or 1;

groups A, D, E, $R_1$, $R_2$ and $R_3$ each denote the same substituent groups as in the formula (1); and groups $R_{11}$ and $R_{12}$ may be the same or different and each denotes a hydrogen atom, a branched or unbranched alkyl group of 1 to 4 carbon atoms, a branched or unbranched haloalkyl group of 1 to 4 carbon atoms, a branched or unbranched alkoxycarbonyl group of 1 to 4 carbon atoms, or a phenyl group optionally having one or more substituent groups listed below. The substituent groups may be the same as or different from one another and is selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group. The exemplified substituent groups may substitute a hydrogen atom at 0 to 5 arbitrary positions of the phenyl group. Specific examples of the above groups are as described hereinabove, but are not limited thereto.

In the substituted pyrazole derivatives of the formula (4), it is preferable that the group A be a phenyl group substituted with 0 to 5 substituent groups (0 substituent group means an unsubstituted phenyl group), the group D be a group selected from branched or unbranched alkyl groups of 1 to 4 carbon atoms, cycloalkyl groups of 3 to 6 carbon atoms and halogen atoms, the group E be a hydrogen atom or a branched or unbranched alkyl group of 1 to 4 carbon atoms, the groups $R_1$ and $R_2$ be hydrogen atoms, the group $R_3$ be a group selected from branched or unbranched alkyl groups of 1 to 4 carbon atoms, alkenyl groups of 2 to 4 carbon atoms, alkynyl groups of 2 to 4 carbon atoms and branched or unbranched alkoxyalkyl groups of 1 to 4 carbon atoms, and the groups $R_{11}$ and $R_{12}$ be the same or different and selected from a hydrogen atom, branched or unbranched alkyl groups of 1 to 4 carbon atoms, branched or unbranched haloalkyl, groups of 1 to 4 carbon atoms and branched or unbranched cyanoalkyl groups of 1 to 4 carbon atoms.

Compounds No. 123 and 124 listed in Table 1 of Examples (presented later) are typical examples of the substituted pyrazole derivatives of the formula (4). However, the inventive compounds are not limited thereto.

Production Process for Substituted Pyrazole Derivatives

A production process for the inventive compounds will be described hereinbelow. To produce the inventive compound (1), the following reaction steps are carried out:

Step (a): A pyrazole derivative of the formula (5) is reacted with a haloalkyleneoxime ester derivative (i.e. oxime derivative of halopyruvate) of the formula (6) in the presence of a base to give an ester derivative of the formula (7):

Step (a):

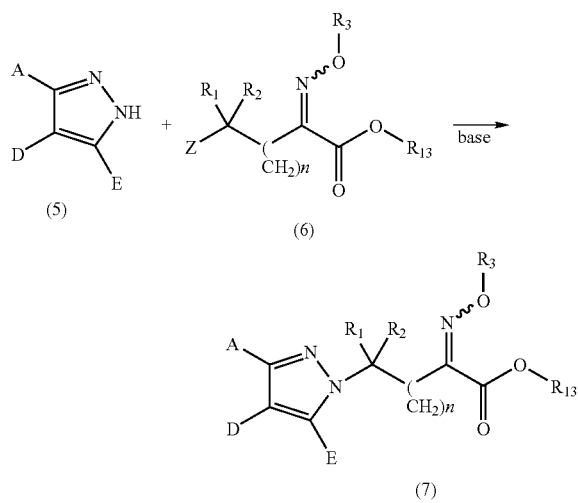

wherein Z is a halogen atom and $R_{13}$ is a methyl or ethyl group.

Step (b): An ester moiety of the ester derivative (formula 7) is hydrolyzed with a base to yield a carboxylic acid derivative represented by the formula (8).

Step (c): The carboxylic acid derivative is reacted with an amine $R_4$—NH—$R_5$ in the presence of a condensation agent to form the inventive compound (formula 1):

Step (b): Step (c):

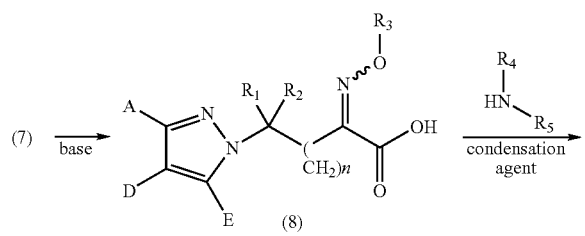

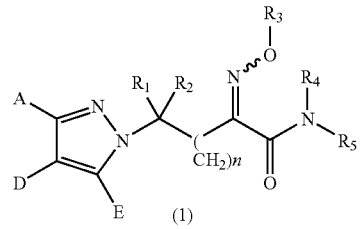

wherein $R_4$ and $R_5$ denote the same groups as described above.

Exemplary condensation agents for use in the Step (c) include carbonyldiimidazole, thionyldiimidazole, dicarboxycarbodiimide and 1-ethyl-3-(3-dimethylaminopropyl)carbodiimide hydrochloride.

Some types of the amines can act on the ester derivative of the formula (7) to directly-synthesize the inventive compound of the formula (1).

Exemplary bases employed in the reaction between the pyrazole derivative of the formula (5) and the haloalkyleneoxime ester derivative of the formula (6) include inorganic bases such as sodium hydride, sodium hydrogencarbonate, sodium carbonate, potassium carbonate and cesium carbonate, and organic bases such as triethylamine and 1,8-diazabicyclo(5,4,0)-undeca-7-ene (DBU).

With respect to the amounts of the reagents subjected to the reaction, about 1 to 5 equivalents, preferably 1 to 3 equivalents of the haloalkyleneoxime ester derivative of the formula (6), and about 1 to 5 equivalents, preferably 1 to 3 equivalents of the base are used per equivalent of the pyrazole derivative represented by the formula (5).

In the above reaction, a solvent is usually used. The solvents employable include ethers such as diethylether, 1,2-dimethoxyethane, tetrahydrofuran, ethylene oxide and 1,4-dioxane; acid amides such as N,N-dimethylformamide and N-methylpyrrolidone; ketones such as acetone, methyl ethyl ketone, methyl isobutyl ketone and cyclohexanone; and acetonitrile.

The reaction temperature and reaction time in the Step (a) are typically about 0 to 150° C., preferably 10 to 100° C., and 10 minutes to 24 hours respectively. The reaction may be followed by conventional treatments and purification by column chromatography, recrystallization or the like as required to prepare the objective compound.

Exemplary bases employable in the Step (b) include lithium hydroxide, potassium hydroxide and sodium hydroxide.

With respect to the amounts of the condensation agent subjected to the reaction, about 1 to 5 equivalents, preferably 1 to 3 equivalents are used, and also about 1 to 5 equivalents, preferably 1 to 3 equivalents of the base are used per equivalent of the ester derivative represented by the formula (7).

In the above reaction, a mixture of water and an alcohol solvent is usually used. The solvents employable include methanol, ethanol, propanol and butanol. The solvent and water are used in equal amounts.

After the reaction, the reaction mixture may be treated by a conventional method, and the reaction product may be separated by column chromatography, recrystallization or the like as required.

The reaction temperature and reaction time in the Step (c) are typically about 0 to 100° C., preferably 10 to 80° C., and 10 minutes to 24 hours respectively.

The substituted pyrazole ring represented by the formula (5) may be synthesized from various pyrazole derivatives having the substituent groups. Exemplary synthesis processes will be given below for the pyrazole rings in which the groups D and E are hydrogen atoms or are substituted, or in which the group D is a halogen atom.

The substituted pyrazole ring of the formula (5) in which E is a hydrogen atom may be obtained by reacting α-formyl ketone of the following formula (9) with hydrazine hydrate (Step (d)). It also results from reaction of an enamine derivative of the formula (10) with hydrazine hydrate (Step (e)).

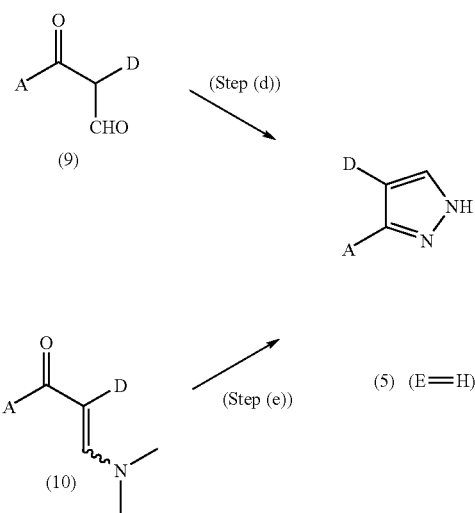

With respect to the amounts of the reagents subjected to the reaction, about 1 to 5 equivalents of the hydrazine hydrate is used per equivalent of the α-formyl ketone of the formula (9) or the enamine derivative of the formula (10).

In the above reaction, a solvent is usually used. The solvents employable include ethers such as diethylether, 1,2-dimethoxyethane and tetrahydrofuran; acid amides such as N,N-dimethylformamide and N-methylpyrrolidone; alcohols such as methanol and ethanol; organic acids such as acetic acid; and aromatic hydrocarbons such as benzene and toluene.

The reaction temperature and reaction time in the Step (d) are typically about 0 to 150° C. and 10 minutes to 24 hours, respectively. The reaction may be followed by a conventional treatment and purification by column chromatography, recrystallization or the like as required to prepare the objective compound.

The α-formyl ketone represented by the formula (9) may be obtained by Claisen condensation between a ketone derivative of the formula (11) and a formate HCOOR$^{14}$ (wherein R$^{14}$ is a methyl or ethyl group) in the presence of a base (Step (f)).

Step (f):

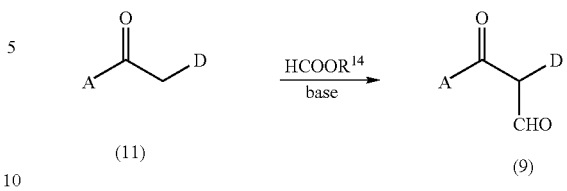

Exemplary bases employable in the above reaction include sodium hydride, sodium methylate and sodium ethylate.

With respect to the amounts of the reagents subjected to the reaction, about 1 to 20 equivalents of the formate and about 1 to 2 equivalents of the base are used per equivalent of the ketone derivative represented by the formula (11).

In the above reaction, a solvent is usually used. Employable solvents include formates. The solvent may be optionally diluted with an ether such as diethylether, 1,2-dimethoxyethane or tetrahydrofuran.

The reaction temperature and reaction time in the Step (f) are typically about 0 to 100° C. and 10 minutes to 24 hours, respectively. The reaction may be followed by a conventional treatment and purification by column chromatography, recrystallization or the like as required to prepare the objective compound.

The enamine derivative of the formula (10) may be obtained by reacting a ketone derivative of the formula (11) with N,N-dimethylformamide dimethylacetal (Step (g)).

Step (g):

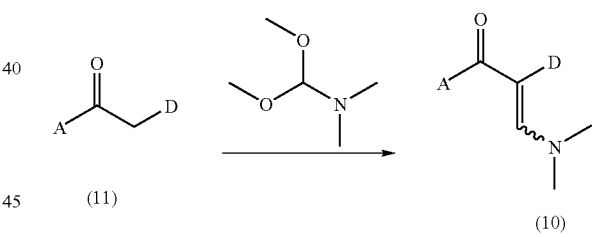

With respect to the amounts of the reagents subjected to the reaction, 1 to 10 equivalents of the N,N-dimethylformamide dimethylacetal is used per equivalent of the ketone derivative represented by the formula (11).

In the above reaction, a solvent is usually used. Exemplary solvents include aromatic hydrocarbons such as benzene and toluene; and ethers such as 1,2-dimethoxyethane and tetrahydrofuran.

The reaction temperature and reaction time in the Step (g) are typically about 0 to 150° C. and 10 minutes to 24 hours, respectively. The reaction may be followed by a conventional treatment and purification by column chromatography, recrystallization or the like as required to prepare the objective compound.

The substituted pyrazole ring of the formula (5) in which E is a substituent group may be obtained by reacting a diketone derivative of the following formula (12) with hydrazine hydrate (Step (h)).

Step (h):

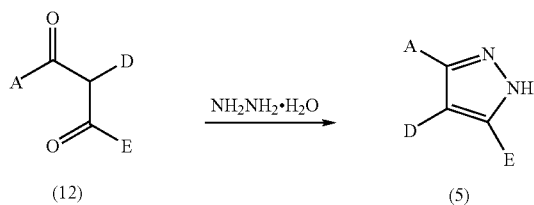

With respect to the amounts of the reagents subjected to the reaction, about 1 to 5 equivalents of the hydrazine hydrate is used per equivalent of the ketone derivative of the formula (12).

In the above reaction, a solvent is usually used. The solvents employable include ethers such as diethylether, 1,2-dimethoxyethane and tetrahydrofuran; acid amides such as N,N-dimethylformamide and N-methylpyrrolidone; alcohols such as methanol and ethanol; organic acids such as acetic acid; and aromatic hydrocarbons such as benzene and toluene.

The reaction temperature and reaction time in the Step (h) are typically about 0 to 150° C. and 10 minutes to 24 hours, respectively. The reaction may be followed by a conventional treatment and purification by column chromatography, recrystallization or the like as required to prepare the objective compound.

The ketone derivative represented by the formula (12) may be obtained by Claisen condensation between a ketone derivative of the formula (11) and a carboxylate in the presence of a base (Step (i)). $R_{15}$ is a $C_{1-4}$ alkyl group.

Step (i):

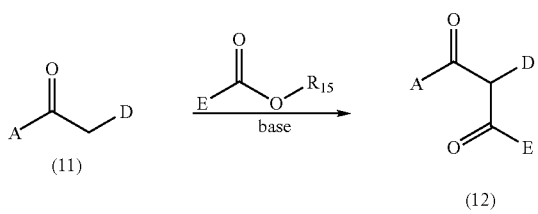

Exemplary bases employable in the above reaction include sodium hydride, sodium methylate and sodium ethylate.

With respect to the amounts of the reagents subjected to the reaction, about 1 to 20 equivalents of the carboxylate and about 1 to 2 equivalents of the base are used per equivalent of the ketone derivative represented by the formula (11).

In the above reaction, a solvent is usually used. Exemplary solvents include ethers such as diethylether, 1,2-dimethoxyethane and tetrahydrofuran; and acid amides such as N,N-dimethylformamide and N-methylpyrrolidone.

The reaction temperature and reaction time in the Step (i) are typically about 0 to 100° C. and 10 minutes to 24 hours, respectively. The reaction may be followed by a conventional treatment and purification by column chromatography, recrystallization or the like as required to prepare the objective compound.

The substituted pyrazole ring of the formula (5) in which D and E are both hydrogen atoms may be obtained by reacting an enamine derivative of the following formula (13) with hydrazine hydrate (Step (j)) to prepare a pyrazole derivative of the formula (5) in which D and E are both hydrogen atoms.

Step (j):

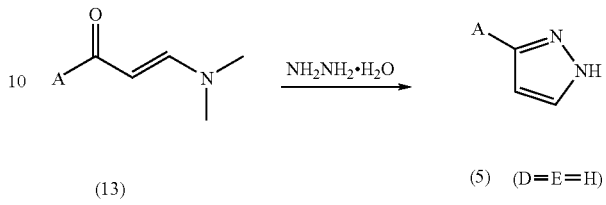

With respect to the amounts of the reagents subjected to the reaction, about 1 to 5 equivalents of the hydrazine hydrate is used per equivalent of the enamine derivative of the formula (13).

In the above reaction, a solvent is usually used. The solvents employable include ethers such as diethylether, 1,2-dimethoxyethane and tetrahydrofuran; acid amides such as N,N-dimethylformamide and N-methylpyrrolidone; alcohols such as methanol and ethanol; organic acids such as acetic acid; and aromatic hydrocarbons such as benzene and toluene.

The reaction temperature and reaction time in the Step (j) are typically about 0 to 150° C. and 10 minutes to 24 hours, respectively. The reaction may be followed by a conventional treatment and purification by column chromatography, recrystallization or the like as required to prepare the objective compound.

The substituted pyrazole ring of the formula (5) in which D is a hydrogen atom may be obtained by reacting a diketone derivative of the following formula (14) with hydrazine hydrate (Step (k)).

Step (k):

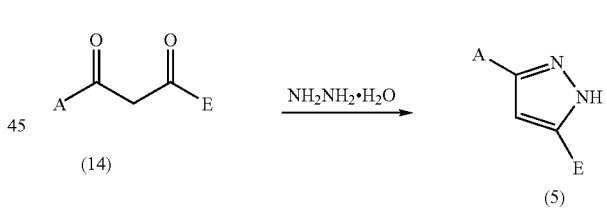

With respect to the amounts of the reagents subjected to the reaction, about 1 to 5 equivalents of the hydrazine hydrate is used per equivalent of the diketone derivative of the formula (14).

In the above reaction, a solvent is usually used. The solvents employable include ethers such as diethylether, 1,2-dimethoxyethane and tetrahydrofuran; acid amides such as N,N-dimethylformamide and N-methylpyrrolidone; and aromatic hydrocarbons such as benzene and toluene.

The reaction temperature and reaction time in the Step (k) are typically about 0 to 150° C. and 10 minutes to 24 hours, respectively. The reaction may be followed by a conventional treatment and purification by column chromatography, recrystallization or the like as required to prepare the objective compound.

The diketone derivative represented by the formula (14) may be obtained by Claisen condensation between a ketone derivative of the formula (15) and a carboxylate in the presence of a base (Step (1)). $R_{16}$ is a $C_{1-4}$ alkyl group.

Step (1):

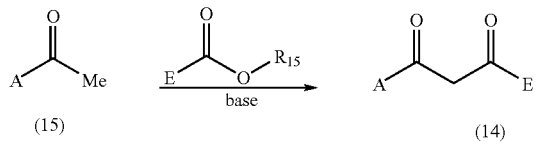

With respect to the amounts of the reagents subjected to the reaction, about 1 to 20 equivalents of the carboxylate and about 1 to 2 equivalents of the base are used per equivalent of the ketone derivative represented by the formula (14).

Exemplary bases employable in the above reaction include sodium hydride, sodium methylate and sodium ethylate.

In the above reaction, a solvent is usually used. Exemplary solvents include ethers such as diethylether, 1,2-dimethoxyethane and tetrahydrofuran; and acid amides such as N,N-dimethylformamide and N-methylpyrrolidone.

The reaction temperature and reaction time in the Step (l) are typically about 0 to 100° C. and 10 minutes to 24 hours, respectively. The reaction may be followed by a conventional treatment and purification by column chromatography, recrystallization or the like as required to recover the reaction product.

The substituted pyrazole ring of the formula (5) in which D is a halogen atom (X) may be obtained by reacting a halogenating agent on a pyrazole derivative of the following formula (16) (Step (m)). X is a chlorine, bromine or iodine atom.

Step (m):

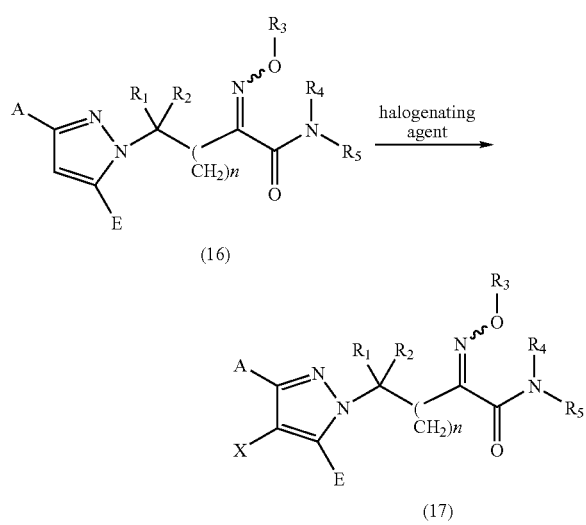

With respect to the amounts of the reagents subjected to the reaction, 1 to 10 equivalents of the halogenating agent is used per equivalent of the pyrazole derivative of the formula (16).

Exemplary halogenating agents include chlorine gas, N-chlorosuccinimide, 1,5-dichloro-5,5-dimethylhydantoin, bromine, N-bromosuccinimide and 1,5-dibromo-5,5-dimethylhydantoin.

In the above reaction, a solvent is usually used. The solvents employable include halogenated solvents such as dichloromethane, chloroform, carbon tetrachloride and 1,2-dichloroethane.

The reaction temperature and reaction time in the Step (m) are typically about 0 to 30° C. and 10 minutes to 24 hours, respectively. The reaction may be followed by a conventional treatment and purification by column chromatography, recrystallization or the like as required to prepare the objective compound.

The haloalkyleneoxime ester derivative represented by the formula (6) may be obtained by reacting a hydroxylamine derivative of the formula (19) with a halopyruvate derivative of the formula (18) (Step (n)).

Step (n):

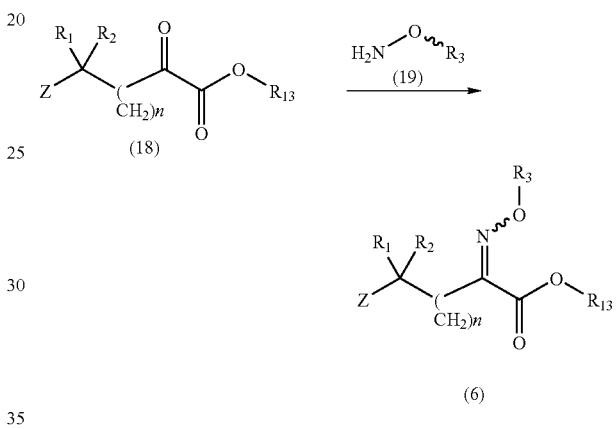

With respect to the amounts of the reagents subjected to the reaction, 1 to 3 equivalents, preferably 1 to 1.5 equivalents of the hydroxylamine of the formula (19) is used per equivalent of the halopyruvate derivative of the formula (18).

In the above reaction, a solvent is usually used. The solvents employable include alcohols such as methanol, ethanol, normal propanol, isopropanol, normal butanol and benzyl alcohol; and aromatic hydrocarbons such as benzene, toluene, xylene, chlorobenzene and ethylbenzene. Of these, methanol, ethanol, benzene and toluene are preferable.

The reaction may be followed by a conventional treatment, and the resultant reaction product may be subjected to the next reaction without purification.

The reaction temperature and reaction time in the above step are typically about 0 to 150° C., preferably 20 to 100° C., and 10 minutes to 24 hours, respectively. The reaction may be followed by a conventional treatment, and the resultant reaction product may be subjected to the next reaction without purification.

The inventive compounds (4) may be obtained according to a similar process to the above synthesis step (c). In this synthesis, the carboxyl acid derivative of the formula (8) is condensed with a substituted hydrazine having substituent groups $R_{11}$ and $R_{12}$ (i.e., $H_2NNR_{11}R_{12}$) in place of the amine $R_4$—NH—$R_5$. Reaction conditions are the same as in the Step (c). Some types of the hydrazine derivatives can act on the ester derivative of the formula (7) to directly synthesize the inventive compound.

Herbicidal Effects

Herbicidal Spectrum (Upland Fields)

Some types of the inventive compounds are useful as upland field and non-crop land herbicides. They, in any treatment among soil treatment, soil incorporation treatment and foliage treatment, can exert in a small dose high herbicidal effects on various species of field weeds. Controllable weeds are, for example, broad leaf-weeds, including Solanaceae weeds such as *Solanum nigrum* and *Datura stramonium*, Malvaceae weeds such as *Abutilon theophrasti* and *Sida spinosa*, Convolvulaceae weeds such as *Ipomoea* spps. (e.g., *Ipomoea purpurea*) and *Calystegia* spps., Amaranthaceae weeds such as *Amaranthus lividus* and *Amaranthus retroflexus*, Compositae weeds such as *Xanthium pensylvanicum*, *Ambrosia artemisiaefolia*, *Helianthus annuus*, *Galinsoga ciliata*, *Cirsium arvense*, *Senecio vulgaris* and *Erigeron annus*, Cruciferae weeds such as *Rorippa indica*, *Sinapis arvensis* and *Capsella Bursapastoris*, Polygonaceae weeds such as *Polygonum Blumei* and *Polygonum convolvulus*, Portulacaceae weeds such as *Portulaca oleracea*, Chenopodiaceae weeds such as *Chenopodium album*, *Chenopodium ficifolium* and *Kochia scoparia*, Caryophyllaceae weeds such as *Stellaria media*, Scrophulariaceae weeds such as *Veronica persica*, Commelinaceae weeds such as *Commelina communis*, Labiatae weeds such as *Lamium amplexicaule* and *Lamium purpureum*, Euphorbiaceae weeds such as *Euphorbia supina* and *Euphorbia maculata*, Rubiaceae weeds such as *Galium spurium* and *Rubia akane*, Violaceae weeds such as *Viola mandshurica*, and Leguminosae weeds such as *Sesbania exaltata* and *Cassia obtusifolia*; and other weeds, including Gramineous weeds such as *Sorghum bicolor*, *Panicum dichotomiflorum*, *Sorghum halepense*, *Echinochloa crus-galli* var. *crus-galli*, *Echinochloa crus-galli* var. *praticola*, *Echinochloa utilis*, *Digitaria adscendens*, *Avenafatua*, *Eleusine indica*, *Setaria viridis*, *Alopecurus aegualis* and *Poa annua*, and Cyperaceous weeds such as *Cyperus rotundus* (*Cyperus esculentus*).

Further, the inventive compounds can control widespread weeds such as those emerging in mowed fields, fallow lands, lands under perennial crops, pastures, lawns, railway sides, athletic grounds, vacant lots, forests, farm lands, levees and other non-crop lands.

Crop Selectivity (Upland Fields)

Some types of the inventive compounds do not adversely affect vegetation of main crops such as *Oryza sativa*, *Triticum aestivum*, *Hordeum vulgare*, *Sorghum bicolor*, *Arachis hypogaea*, *Zea mays*, *Glycine max*, *Gossypium* spp. and *Beat vulgaris*, lawn grasses such as *Zoysia japonica* and *Zoysia matrella*, and garden crops such as flowers, ornamental plants and vegetable crops including *Raphanus sativus* and *Brassica napus*.

Herbicidal Spectrum (Paddy Fields)

Some types of the inventive compounds are useful as paddy field herbicides. They, in any treatment of waterlogged soil treatment and foliage treatment, can exert in a small dose high herbicidal effects on various species of paddy weeds. Such weeds are, for example, Alismataceae weeds such as *Alisma canaliculatum*, *Sagittaria trifolia* and *Sagittaria pygmaea*, Cyperaceous weeds such as *Cyperus difformis*, *Cyperus serotinus*, *Scirpus juncoides*, *Eleocharis kuroguwai* and *Eleocharis acicularis*, Scrophulariaceae weeds such as *Lindernia pyxidaria*, Pontederiaceae weeds such as *Monochoria vaginalis*, Potamogetonaceae weeds such as *Potamogeton distihctus*, Umbelliferae weeds such as *Oenanthe javanica*, Lythraceae weeds such as *Rotala indica* and *Ammannia multiflora*, Elatinaceae weeds such as *Elatine triandra*, and Graminaceous weeds such as *Echinochloa oryzicola*, *Echinochloa crus-galli* var. *formosensis* and *Echinochloa crus-galli* var. *crus-galli*.

Crop Selectivity (Paddy Rice)

The inventive compounds do not pose a significant chemical hazard to transplantation paddy rice or direct-sowing paddy rice.

Effect on Aquatic Plants

The inventive compounds exhibit an efficacy onalgae such as blue-green algae, and aquatic weeds such as *Eichhornia crassipes*, which emerge in creeks, canals, lakes, marshes, ponds and water reservoirs.

Formulations

The herbicide compositions according to the present invention contain one or more kinds of the inventive compounds as active ingredients. In the formulation of the compositions, the active ingredient(s) is (are) combined with a solid or liquid carrier and optionally with a surfactant and other adjuvant, and the mixture is formulated into conventional forms of agricultural chemicals, such as wettable powders, powders, granules, pellets, concentrated liquids, aerosols, water-soluble powders, emulsifiable concentrates, suspension concentrates, flowables and packs. For application in paddy fields in particular, the herbicide composition is favorably formulated into granules and packed in a water-soluble polymer film as will be described later.

For the preparation of the herbicide compositions, any process conventionally used in formulation of agricultural chemicals may be employed. If necessary, the active ingredients for the agricultural chemicals may be finely pulverized in advance by an air mill or a hummer mill, and mixed with a carrier, a surfactant or the like. To produce formulations other than powders, appropriate treatment may be performed depending on the type of the objective formulation. In the case of granule formulations, for example, required ingredients may be mixed, kneaded and granulated to the desired size with an extruder according to a common granulation method for granular agricultural chemicals. For the preparation of suspension formulations, the active ingredient(s) may be dispersed into water containing a carrier and a surfactant as wetting agent, dispersing agent and suspending agent, and the suspended particles may be ground by a wet grinding mill such as DYNO-Mill or sand grinder and optionally mixed with an adjuvant or the like. The water-soluble powders and wettable powders may be dissolved or suspended in water for application. The emulsifiable concentrates may be prepared by mixing the active ingredient(s) with an appropriate emulsifying agent by a homogenizer, a pressure emulsifier or DYNO-Mill.

Additives

In the practical application of the inventive compounds, the compounds may be used as they are. They may also be employed as compositions in combination with useful additives generally used for formulation, such as carriers, surfactants, solvents, and adjuvants effective for enhancing dispersion and for improving other properties of the active ingredients (e.g., thickening agents, antifreezing agents, anti-foaming agents, antiseptic agents, stabilizing agents and colorants).

Examples of the solid carriers or diluents include fine powders or granules of plant substances, fibrous materials, synthetic plastic powders, clays (such as kaolin, bentonite, terra abla, diatomaceous earth and Fubasami clay), talcs, inorganic materials (pumice, powdered sulfur, active carbon and calcium carbonate), and chemical fertilizers (such as ammonium sulfate, ammonium phosphate and urea). Examples of the liquid carriers or diluents include water, alcohols, ketones, ethers, aromatic hydrocarbons, aliphatic hydrocarbons, esters, nitrites, amides (N,N-dimethylformamide, dimethyl sulfoxide), and halogenated hydrocarbons.

Examples of the surfactants include alkylsulfuric acid esters, alkyl sulfonates, alkylarylsulfonic acids, alkylaryl. ethers, polyethylene glycol ethers, polyhydric alcohol esters and sugar alcohol derivatives.

Examples of the spreading or dispersing agents include casein, gelatin, starch powders, carboxymethylcellulose, gum arabic, alginic acid, lignin, bentonite, polyvinylalcohol, pineapple oil, molasses and agar and the like.

Examples of the stabilizers include isopropylphosphate mixtures, tricresyl phosphate, tall oil, epoxy oil, surface-active agents, fatty acids and esters thereof. As will be described later, the formulations according to the present invention may contain other fungicides, insecticides, herbicides or fertilizers in addition to the above ingredients.

Active Ingredient Concentrations

The concentrations of the active ingredients in the herbicide compositions of the invention can be variously changed depending on the formulation forms as described above. In the case of the wettable powders, the active ingredient concentration is in the range of 5 to 90%, and preferably about 10 to 85%. For the emulsifiable concentrates, the active ingredient concentration is in the range of 3 to 70%, and preferably about 5 to 60%. For the granules, the active ingredient concentration is in the range of 0.01 to 50%, and preferably about 0.05 to 40%.

Usage (Dosage and Application Method)

Wettable powders or emulsifiable concentrates thus formulated may be sprayed or incorporated as suspensions or emulsions diluted with water to a given concentration, before or after sprouting of the target weeds. Granule formulations can be directly applied or incorporated as such before or after sprouting of the target weeds. In practical application of the herbicide composition of the invention as a herbicide, it will be appropriately used in such an amount that gives not less than 0.1 g of the active ingredient(s) per hectare.

When the inventive compound is used as an active ingredient of a herbicide, the amount thereof is usually in the range of 10 g to 8000 g, preferably 10 g to 2000 g per hectare, although it varies with meteorological conditions, formulation forms, application times, application methods, soil conditions, crops in cultivation, target weeds, etc. In the case of emulsifiable concentrates, wettable powders, suspension concentrates, concentrated emulsions, water-dispersible granules, liquid formulations and the like, given amounts of such formulations are applied after usually diluted with 10 to 1000 liters of water (optionally containing adjuvants such as a spreader) per hectare. On the other hand, granules and some types of suspension concentrates and liquid formulations are generally applied without any dilution. Examples of the adjuvants include the surfactants described above, polyoxyethylene fatty acids (esters), lignin-insulfonates, abietates, dinaphthylmethanedisulfonate, and vegetable oils such as crop oil concentrate, soybean oil, corn oil, cotton seed oil and sunflower oil.

Combination Use

The herbicide compositions of the invention may be used as mixtures with one or more plant protecting agents, such as fungicides, insecticides, herbicides, nematicides, acaricides, bactericides, plant growth regulators, fertilizers and soil improvers.

The inventive compounds may be used in combination with a compound(s) that shows growth controlling or regulating activities on valuable plants such as crops, ornamental plants and fruit trees. Such plant growth controlling compounds include, but not limited to, ethephon, indoleacetic acid, ethychlozate, cloxyfonac, dichlorprop, 1-naphthylacetamide, 4-CAP, benzylaminopurine, forchlorfenuron, gibberellin, maleic hydrazide, inabenfide, uniconazole-P, chlormequat, paclobutrazole, flurprimidol, mepiquat chloride, prohexadione calcium, trinexapac ethyl, daminozide, mefluidide, isoprothiolane and oxine sulfate. These may be used singly or as a mixture of two or more kinds.

Examples of the fungicides include, but not limited to, phthalide, flutolanil, mepronil, S-658, pyroquilon, tricyclazole, probenazole, isoprothio-lane, iprobenfos, tecloftalam and benomyl. Examples of the insecticides include, but not limited to, isoxathion, trichlorophon, propaphos, diazinon, formothion, disulfoton, dimethoate, monocrotophos, acephate, carbofuran, carbosulfan, thiocyclam, cartap, bensultap, benfuracarb, furathibcarb, carbaryl, buprofezin, fenobucarb, metolcarb, propoxur, methomyl, imidacloprid, nitenpyram, cycloprothrin, ethofenprox and silafluofen. These may be used singly or as a mixture of two or more kinds.

Herbicide Mixture

Usage of the herbicide composition as mixed further with other herbicidal component brings about reduction in application dose and labor saving for application. Owing to synergy effects of such mixed herbicides, wider herbicidal spectrum and higher herbicidal performance can be expected in the herbicide composition as described herein. The herbicide composition may be mixed with two or more known herbicides. Such herbicides include atrazine, cyanazine, dimethametryn, metribuzin, prometryn, simazine, simetryn, chlortoluron, diuron, daimuron, fluometuron, isoproturon, linuron, methabenzthiazuron, amicarbazone, bromoxynil, ioxynil, ethalfluralin, pendimethalin, trifluralin, acifluorfen, acifluorfen-sodium, bifenox, chlomethoxynil, fomesafen, lactofen, oxadiazon, oxadiargyl, oxyfluorfen, carfentrazone-ethyl, flumiclorac-pentyl, flumioxazine, fluthiacet-methyl, sulfentrazone, thidiazimin, azafenidin, pyraflufen-ethyl, cinidon-ethyl, difenzoquat, diquat, paraquat, 2,4-D, 2,4-DB, DCPA, MCPA, MCPB, clomeprop, clopyralid, dicamba, dithiopyr, fluroxypyr, mecoprop, naploanilide, phenothiol, quinclorac, triclopyr, thiazopyr, acetochlor, alachlor, butachlor, diethatyl-ethyl, metolachlor, pretilachlor, propachlor, bensulfuron-methyl, chlorsulfuron, chlorimuron-ethyl, halosulfuron-methyl, metsulfuron-methyl, nicosulfuron, primisulfuron-methyl, pyrazosulfuron-ethyl, sulfometuron-ethyl, thifensulfuron-methyl, triasulfuron, tribenuron-methyl, oxasulfuron, azimsulfuron, cloransulam-methyl, cyclosulfamuron, flumetsulam, florasulam, flupyrsulfuron, flazasulfuron, imazosulfuron, metosulam, diclosulam, prosulfuron, rimsulfuron, triflusulfuron-methyl, ethoxysulfuron, sulfosulfuron, flucarbazone-sodium, procarbazone-sodium (MKH-6561), imazamethabenz-methyl, imazapyr, imazaquin, imazethapyr, imazameth, imazamox, bispyribac-sodium, pyriminobac-methyl, pyrithiobac-sodium, alloxydim-sodium, clethodim, sethoxydim, tralkoxydim, tepraloxydim, profoxydim (BAS-625H), diclofop-methyl, fenoxaprop-ethyl, fenoxaprop-p-ethyl, fluazifop-buthyl, fluazifop-p-butyl, haloxyfop-methyl, quizalofop-p-ethyl, cyhalofop-butyl, clodinafop-propargyl, benzofenap, clomazone, diflufenican, norflurazone, pyrazolate, pyrazoxyfen, picolinafen, beflubutamid, flurtamone, isoxaflutole, sulcotrione, benzobicyclon, mesotrione, glufosinate-ammonium, glyphosate, bentazone, benthiocarb, bromobutide, butamifos, butylate, dimepiperate, dimethenamid, DSMA, EPTC, esprocarb, isoxaben, mefenacet, molinate, MSMA, piperophos, pyributicarb, prosulfocarb, propanil, pyridate, triallate, cafenstrol, flupoxam, flufenacet, diflufenzopyr, triaziflam, pentoxazone, indanofan, metobenzuron, oxaziclomefone and fentrazamide.

These compounds are described in a catalog of Farm Chemical Handbook (Meister Publishing Company) (1997), SHIBUYA INDEX (8th edition) (1999), The Pesticide Manual (British crop protection council) 12th edition (2000), and Herbicide research conspectus (Hakuyu-sha). The above listed compounds are just illustrative and not exclusive. The compounds may be used singly or as a mixture of two or more kinds.

The appropriate mixing ratio between the inventive compound and other herbicide(s) may vary depending on the type of active ingredients of the additional herbicide (s). However, it is generally in the range of 1:0.01 to 1:10, by weight. When the herbicide compositions of the invention are used with the aforesaid other herbicide(s), the formulation process is not specifically restricted. For example, the inventive compound and other active ingredient(s) such as the aforesaid additional herbicide(s) are each previously mixed with a solid carrier, a liquid carrier, a surfactant or other adjuvant to give emulsifiable concentrates, wettable powders, suspension concentrates, water-soluble granules, water-soluble powders, aqueous solutions, water-dispersible granules or the like, followed by mixing together. It is also possible that the inventive compound is premixed with the additional herbicide(s) and thereafter the admixture is mixed with a solid carrier, a liquid carrier, a surfactant or other formulation adjuvant to yield an emulsifiable concentrate, wettable powder, a suspension concentrate, granules, a concentrated emulsion, water-dispersible granules or the like. The resulting formulations will contain the inventive compound and other herbicides as active ingredients in a total amount of 0.5 to 80% by weight, preferably 1.5 to 70% by weight.

Application Method

The formulated compositions of the present invention may be applied to plants to be controlled directly or after diluted with water or the like. The application may be performed according to a variety of methods. Exemplary application techniques are spraying or spreading, application of creamlike- or paste-formulated herbicides, vapor application, and application of slow release granular herbicides.

The herbicide compositions of the invention can treat plants by being directly sprayed, spread or applied onto the targets, or by being spread over or incorporated in the soil around the plants, paddy field, etc. In the case of paddy fields, any application methods may be employed, such as carrying the herbicide composition with the flow of agricultural water from a water intake, dropping the composition from a levee into the paddy field and allowing it to spread, or setting the composition to a transplanting machine of rice seedlings in a manner adapted for the herbicide application.

When the herbicide composition is to be applied on a water surface, an embodiment of the invention where the herbicide composition is filled and packed in a water-soluble or water-degradable bag is preferable from the viewpoint of handling and application. When such floatable packs are dispersed on a waterlogged field, they favorably float on the water surface and spread (diffuse) away. Consequently, the active ingredients of the herbicide can be uniformly dispersed over or into the paddy field. Therefore, reduction can be achieved in labor of herbicide application and phytotoxicity, and stable effects can be expected.

In order that the herbicide composition become capable of floating on the water surface, it is required that either the specific gravity of the composition is regulated to less than 1.0, preferably 0.95 or less, or the composition contains a foaming agent such as a carbonate and a water-soluble solid acid.

In application of the herbicide formulation of the invention in which the herbicide composition is packed in a water-soluble or water-degradable bag, the desired aim can be accomplished only by dropping the formulation directly in a waterlogged field in a ratio of 3 to 20 packs per 10a. Dropped in water, these packs will diffuse afloat on the water surface, otherwise submerge once but soon resurface and diffuse afloat on the water surface, or diffuse while repeatedly submerging and soon resurfacing, i.e., they submerge but soon resurface and diffuse afloat on the water surface again and again. Generally, floatable herbicide formulations of such a type that they submerge and then resurface are capable of quick resurfacing and unlikely to become captured on the soil surface. As described above, the formulations of the present invention have excellent spreadability (diffusion properties) and diffuse evenly over the paddy field. These attributes allow the applicator to achieve uniform dispersion of the formulations even without stepping into the paddy field, and labor can be reduced. Accordingly, the above floatable formulations of the herbicide composition are a preferred embodiment of the present invention.

EXAMPLES

The present invention is further described with reference to the following examples and test examples, but it should be construed that the invention is in no way limited to those examples.

In the following description, the term "part(s)" means "part(s) by weight".

Synthesis of Pyrazole Derivatives

Hereinbelow, synthesis of the inventive compounds represented by the formula (1) or (4) will be illustrated in detail by examples.

Production Example 1

Synthesis of ethyl 2-methoxyimino-3-bromopropionate (represented by the formula (6) in the Step (n) in which n is 0, $R_1$ and $R_2$ are both hydrogen atoms, Z is a bromine atom, $R_3$ is a methoxy group and $R_{13}$ is ethyl)

Ethyl bromopyruvate (80% purity), 38.9 g (200 mmol as calculated on an assumption of 100% purity) was dissolved in 100 ml of ethanol. At room temperature, 16.6 g (200 mmol) of methoxyamine hydrochloride was added to the solution, followed by heating under reflux for 2 hours. After reaction had been completed, ethanol was distilled away, and 200 ml of ethyl acetate was added to the residue. The reaction product was washed sequentially with a saturated aqueous solution of sodium hydrogencarbonate and an aqueous solution of sodium chloride, and then dried over anhydrous magnesium sulfate. Filtration and subsequent distillation to remove the solvent gave 36.9 g (165 mmol) of ethyl 2-methoxyimino-3-bromopropionate as a light yellow oily matter. The yield was 80%. The product synthesized was subjected to the next reaction without purification.

Production Example 2

Synthesis of 2-methoxyimino-3-((4'-methoxyphenyl)-4-methyl-pyrazole)-1-yl-propanoic acid-N-methylamide (Compound No. 41 represented by the formula (1) in which n is 0, A is 4-methoxyphenyl, D is methyl, E is a hydrogen atom, $R_1$ and $R_2$ are both hydrogen atoms, $R_3$ is methyl, $R_4$ is a hydrogen atom and $R_5$ is methyl)

(Step 1)

10 g (60.9 mmol) of 4'-methoxypropiophenone was dissolved in 100 ml of methyl formate. At room temperature, sodium methoxide, 15.3 g (79.2 mmol) at a concentration of 28% in methanol solution was dropwise added to the solution over a period of 30 minutes, followed by stirring at the same temperature for 6 hours. To the reaction mixture was added 100 ml of water, and the solution pH was adjusted to 1 with concentrated hydrochloric acid, followed by stirring for further 1 hour. Thereafter, the reaction mixture was extracted with 100 ml of ethyl acetate three times. The organic phase was washed with a saturated aqueous solution of sodium chloride and then dried over anhydrous magnesium sulfate. Filtration and subsequent distillation to remove the solvent gave 9.8 g (51.0 mmol) of 2-formyl-4'-methoxypropiophenone as a light yellow crystal. The yield was 84%. The product synthesized was subjected to the next reaction without purification.

(Step 2)

9.8 g (51.0 mmol) of the 2-formyl-4'-methoxypropiophenone synthesized in Step 1 was dissolved in 150 ml of ethanol. At room temperature, 3.8 g (61.2 mmol) of 80% hydrazine hydrate was dropwise added to the solution, followed by stirring at the same temperature for 1 hour and further by heating under reflux for 2 hours. After reaction had been completed, the reaction mixture was cooled to room temperature and the solvent was distilled away. As a result, 8.4 g (44.9 mmol) of 3-(4'-methoxyphenyl)-4-methylpyrazole was obtained as an orange oily matter. The yield was 88%. The product synthesized was subjected to the next reaction without purification.

(Step 3)

1.6 g (8.5 mmol) of the 3-(4'-methoxyphenyl)-4-methylpyrazole synthesized in Step 2 was dissolved in 30 ml of N,N-dimethylformamide. At room temperature, 1.4 g (10.2 mmol) of potassium carbonate and 2.9 g (10.2 mmol) of the ethyl 2-methoxyimino-3-bromopropionate synthesized in Production Example 1 were sequentially added to the solution, followed by heating at 110° C. under stirring for 4 hours. After reaction had been completed, the reaction mixture was poured into 100 ml of water, and was extracted with 50 ml of diethylether three times. The organic-phase was washed with a saturated aqueous solution of sodium chloride and then dried over anhydrous magnesium sulfate. Filtration and subsequent distillation to remove the solvent gave 2.6 g (7.4 mmol) of ethyl 2-methoxyimino-3-((4'-methoxyphenyl)-4-methyl-pyrazole)-1-yl-propanoate in a 100 ml three-necked flask. The yield was 87%. The product synthesized was subjected to the next reaction without purification.

(Step 4)

1.1 g (3.1 mmol) of the ethyl 2-methoxyimino-3-((4'-methoxyphenyl)-4-methyl-pyrazole)-1-yl-propanoate synthesized in Step 3 was combined with a methanol solution of 40% methylamine, followed by stirring at room temperature for 4 hours. After reaction had been completed, the solvent was distilled away. The resultant residue was purified by silica gel column chromatography using chloroform as an eluting solution. Subsequently, the solvent was removed by distillation to yield 0.96 g (2.9 mmol) of 2-methoxyimino-3-((4'-methoxyphenyl)-4-methyl-pyrazole)-1-yl-propanoic acid-N-methylamide as a white crystal. The yield was 94%.

Production Example 3

Synthesis of 2-methoxyimino-3-((2',6'-difluorophenyl)-4-methyl-pyrazole)-1-yl-propanoic acid-N-methylamide (Compound No. 58 represented by the formula (1) in which n is 0, A is 2, 6-difluorophenyl, D is methyl, E is a hydrogen atom, $R_1$ and $R_2$ are both hydrogen atoms, $R_3$ is methyl, $R_4$ is a hydrogen atom and $R_5$ is methyl)

(Step 1)

4.9 g (29.0 mmol) of 2,6-difluoropropiophenone was dissolved in 100 ml of toluene. To the solution, 6.9 g (58.0 mmol) of N,N-dimethylformamide dimethylacetal was added, followed by heating under reflux for 8 hours and further by stirring at the same temperature for 6 hours. After reaction had been completed, the toluene and excess of N,N-dimethylformamide dimethylacetal were distilled away to yield 6.2 g (27.5 mmol) of 1-(2',6'-difluorophenyl)-2-methyl-3-N,N-dimethylamino-2-propene as an orange resinous substance. The yield was 95%.

(Step 2)

6.2 g (27.5 mmol) of the 1-(2',6'-difluorophenyl)-2-methyl-3-N,N-dimethylamino-2-propene synthesized in Step 1 was dissolved in 150 ml of ethanol. At room temperature, 2.4 g (37.7 mmol) of 80% hydrazine hydrate was dropwise added to the solution, followed by stirring at the same temperature for 1 hour and further by heating under reflux for 2 hours. After reaction had been completed, the reaction mixture was cooled to room temperature and the solvent was distilled away. As a result, 4.8 g (24.7 mmol) of 3-(2',6'-difluorophenyl)-4-methylpyrazole was obtained as an orange oily matter. The yield was 85%. The product synthesized was subjected to the next reaction without purification.

(Step 3)

2.0 g (10.0 mmol) of the 3-(2',6'-difluorophenyl)-4-methylpyrazole synthesized in Step 2 was dissolved in 40 ml of N,N-dimethylformamide. At room temperature, 1.7 g (12.0 mmol) of potassium carbonate and 3.5 g (12.4 mmol) of the ethyl 2-methoxyimino-3-bromopropionate synthesized in Production Example 1 were sequentially added to the solution, followed by heating at 110° C. under stirring for 4 hours. After reaction had been completed, the reaction mixture was poured into 100 ml of water, and was extracted with 50 ml of diethylether three times. The organic phase was washed with a saturated aqueous solution of sodium chloride and then dried over anhydrous magnesium sulfate. Filtration and subsequent distillation to remove the solvent gave 2.6 g (7.7 mmol) of ethyl 2-methoxyimino-3-((2',6'-difluorophenyl)-4-methyl-pyrazole)-1-yl-propanoate. The yield was 62%. The product synthesized was subjected to the next reaction without purification.

(Step 4)

2.6 g (7.7 mmol) of the ethyl 2-methoxyimino-3-((2',6'-difluorophenyl)-4-methyl-pyrazole)-1-yl-propanoate synthesized in Step 3 was combined with 30 ml of a methanol solution of 40% methylamine, followed by stirring at room temperature for 4 hours. After reaction had been completed, the solvent was distilled away. The residue was purified by silica gel column chromatography using chloroform as an eluting solution. Subsequently, the solvent was removed by distillation to yield 2.0 g (6.2 mmol) of 2-methoxyimino-3-

((2',6'-difluorophenyl)-4-methyl-pyrazole)-1-yl-propanoic acid-N-methylamide as a white crystal. The yield was 81%.

Production Example 4

Synthesis of 2-methoxyimino-3-(phenyl-4-methyl-pyrazole)-1-yl-propanoic acid-N-cyclopropylamide (Compound No. 21 represented by the formula (1) in which n is 0, A is phenyl, D is methyl, E is a hydrogen atom, $R_1$ and $R_2$ are both hydrogen atoms, $R_3$ is methyl, $R_4$ is a hydrogen atom and $R_5$ is cyclopropyl)

(Step 1)

5.0 g (37.3 mmol) of propiophenone was dissolved in 100 ml of methyl formate. At room temperature, 8.6 g (44.7 mmol) of a methanol solution of 28% sodium methoxide was dropwise added to the solution over a period of 30 minutes, followed by stirring at the same temperature for 6 hours. To the reaction mixture was added 100 ml of water, and the solution pH was adjusted to 1 with concentrated hydrochloric acid, followed by stirring for further 1 hour. Thereafter, the reaction mixture was extracted with 100 ml of ethyl acetate three times. The organic phase was washed with a saturated aqueous solution of sodium hydrochloride and then dried over anhydrous magnesium sulfate. Filtration and subsequent distillation to remove the solvent gave 5.7 g (35.4 mmol) of 2-formylpropiophenone as a light yellow crystal. The yield was 95%. The product synthesized was subjected to the next reaction without purification.

(Step 2)

5.7 g (35.4 mmol) of the 2-formylpropiophenbne synthesized in Step 1 was dissolved in 150 ml of ethanol. At room temperature, 2.4 g (37.7 mmol) of 80% hydrazine hydrate was dropwise added to the solution, followed by stirring at the same temperature for 1 hour and further by heating under reflux for 2 hours. After reaction had been completed, the reaction mixture was cooled to room temperature and the solvent was distilled away. As a result, 5.2 g (33.2 mmol) of 3-phenyl-4-methylpyrazole was obtained as a white crystal. The yield was 88%. The product synthesized was subjected to the next reaction without purification.

(Step 3)

2.0 g (12.7 mmol) of the 3-phenyl-4-methylpyrazole synthesized in Step 2 was dissolved in 40 ml of N,N-dimethylformamide. At room temperature, 2.1g (15.2 mmol) of potassium carbonate and 3.4 g (15.2 mmol) of the ethyl 2-methoxyimino-3-bromopropionate synthesized in Production Example 1 were sequentially added to the solution, followed by heating at 110° C. under stirring for 4 hours. After reaction had been completed, the reaction mixture was poured into 100 ml of water, and was extracted with 50 ml of diethylether three times. The organic phase was washed with a saturated aqueous solution of sodium hydrochloride and then dried over anhydrous magnesium sulfate. Filtration and subsequent distillation to remove the solvent gave 2.9 g (9.6 mmol) of ethyl 2-methoxyimino-3-(phenyl-4-methyl-pyrazole)-1-yl-propanoate. The yield was 63%. The product synthesized was subjected to the next reaction without purification.

(Step 4)

2.9 g (9.6 mmol) of the ethyl 2-methoxyimino-(3-phenyl-4-methyl-pyrazole)-1-yl-propanoate synthesized in Step 3 was dissolved in a mixed solvent consisting of 20 ml of ethanol and 20 ml of water. At room temperature, 0.5 g (9.6 mmol) of potassium hydroxide powder (85%) was added to the solution, followed by stirring at the same temperature for 1 hour. After reaction had been completed, the pH of the reaction mixture was adjusted to 1 with concentrated hydrochloric acid. Thereafter, the reaction mixture was extracted with 50 ml of ethyl acetate three times. The organic phase was washed with a saturated aqueous solution of sodium hydrochloride and then dried over anhydrous magnesium sulfate. Filtration and subsequent distillation to remove the solvent gave 2.6 g (9.5 mmol) of 2-methoxyimino-3-(phenyl-4-methylpyrazole)-1-yl-propanoic acid. The yield was 99%. The product synthesized was subjected to the next reaction without purification.

(Step 5)

2.1 g (7.7 mmol) of the 2-methoxyimino-3-(phenyl-4-methylpyrazole)-1-yl-propanoic acid synthesized in Step 4 was dissolved in 30 ml of tetrahydrofuran. At room temperature, 1.9 g (11.5 mmol) of carbonyldiimidazole was added to the solution, followed by stirring at the same temperature for 30 minutes. Subsequently, 1.3 g (23.1 mmol) of cyclopropylamine was added, and the mixture was stirred at the same temperature for 2 hours. After reaction had been completed, the reaction mixture was poured into 50 ml of water, and was extracted with 50 ml of diethylether three times. The organic phase was dried over anhydrous magnesium sulfate, followed by filtration and distillation to remove the solvent. The residue was purified by silica gel column chromatography using chloroform as an eluting solution. Subsequently, the solvent was removed by distillation to yield 1.0 g (3.2 mmol) of 2-methoxyimino-3-(phenyl-4-methyl-pyrazole)-1-yl-propanoic acid-N-cyclopropylamide as a white crystal. The yield was 42%.

Compounds Nos. 1–20, 22–40, 42–57 and 59–124 listed in Table 1 were further prepared in addition to the compounds Nos. 41 (Production Example 2), 58 (Production Example 3) and 21 (Production Example 4). They were synthesized by the procedures illustrated in Production Examples 1 to 4, except that the starting materials were altered to compounds having corresponding groups to those in the objective compounds. NMR spectrum data and physical properties of these compounds are shown in Tables 2 and 3 respectively.

In Table 1, Ph, Me, Et, Bn, Pr, Bu, Pen, Hex, 1, c and t denote phenyl, methyl, ethyl, benzyl, propyl, butyl, pentyl, hexyl, linear, cyclic and tertiary respectively.

TABLE 1

| No. | A | D | E | R1 | R2 | R3 | R4 | R5 | n |
|---|---|---|---|---|---|---|---|---|---|
| 1 | H | Me | H | H | H | Me | H | Me | 0 |
| 2 | Me | Me | H | H | H | Me | H | Me | 0 |
| 3 | Et | Me | H | H | H | Me | H | Me | 0 |
| 4 | n-Pr | Me | H | H | H | Me | H | Me | 0 |
| 5 | i-Pr | Me | H | H | H | Me | H | Me | 0 |
| 6 | c-Pr | Me | H | H | H | Me | H | Me | 0 |
| 7 | n-Bu | Me | H | H | H | Me | H | Me | 0 |
| 8 | t-Bu | Me | H | H | H | Me | H | Me | 0 |
| 9 | c-Bu | Me | H | H | H | Me | H | Me | 0 |
| 10 | c-Pen | Me | H | H | H | Me | H | Me | 0 |

TABLE 1-continued

| No. | A | D | E | R1 | R2 | R3 | R4 | R5 | n |
|---|---|---|---|---|---|---|---|---|---|
| 11 | c-hex | Me | H | H | H | Me | H | Me | 0 |
| 12 | CF$_3$ | Me | H | H | H | Me | H | Me | 0 |
| 13 | Ph | H | H | H | H | Me | H | Me | 0 |
| 14 | Ph | Cl | H | H | H | Me | H | Me | 0 |
| 15 | 4-F—Ph | ethynyl | H | H | H | Me | H | Me | 0 |
| 16 | Ph | Me | H | H | H | Me | H | H | 0 |
| 17 | 4-Cl—Ph | Me | H | H | H | Me | H | H | 0 |
| 18 | Ph | Me | H | H | H | Me | H | Me | 0 |
| 19 | Ph | Me | H | H | H | Me | H | Et | 0 |
| 20 | Ph | Me | H | H | H | Me | H | I—Pr | 0 |
| 21 | Ph | Me | H | H | H | Me | H | c-Pr | 0 |
| 22 | Ph | Me | H | H | H | Me | H | t-Bu | 0 |
| 23 | Ph | Me | H | H | H | Me | H | c-Pen | 0 |
| 24 | Ph | Me | H | H | H | Me | H | c-Hex | 0 |
| 25 | Ph | Me | H | H | H | Me | H | 2-Me-c-Hex | 0 |
| 26 | Ph | Me | H | H | H | Me | H | 2-Propenyl | 0 |
| 27 | Ph | Me | H | H | H | Me | H | 2-Propynyl | 0 |
| 28 | Ph | Me | H | H | H | Me | H | 2,2-(OEt)$_2$-Ethyl | 0 |
| 29 | Ph | Me | H | H | H | Me | H | Ph | 0 |
| 30 | Ph | Me | H | H | H | Me | H | Bn | 0 |
| 31 | Ph | Me | H | H | H | Me | H | α-Fenethyl | 0 |
| 32 | Ph | Me | H | H | H | Me | H | 3',4'-(OMe)$_2$-β-Fenethyl | 0 |
| 33 | Ph | Me | H | H | H | Me | H | CH$_2$CN | 0 |
| 34 | Ph | Me | H | H | H | Me | H | CH$_2$CF$_3$ | 0 |
| 35 | 2-Me—Ph | Me | H | H | H | Me | H | Me | 0 |
| 36 | 3-Me—Ph | Me | H | H | H | Me | H | Me | 0 |
| 37 | 4-Me—Ph | Me | H | H | H | Me | H | Me | 0 |
| 38 | 4-i-Pr—Ph | Me | H | H | H | Me | H | Me | 0 |
| 39 | 4-Ph—Ph | Me | H | H | H | Me | H | Me | 0 |
| 40 | 4-CF$_3$—Ph | Me | H | H | H | Me | H | Me | 0 |
| 41 | 4-OMe—Ph | Me | H | H | H | Me | H | Me | 0 |
| 42 | 2-F—Ph | Me | H | H | H | Me | H | Me | 0 |
| 43 | 3-F—Ph | Me | H | H | H | Me | H | Me | 0 |
| 44 | 4-F—Ph | Me | H | H | H | Me | H | Me | 0 |
| 45 | 2-Cl—Ph | Me | H | H | H | Me | H | Me | 0 |
| 46 | 3-Cl—Ph | Me | H | H | H | Me | H | Me | 0 |
| 47 | 4-Cl—Ph | Me | H | H | H | Me | H | Me | 0 |
| 48 | 2-Br—Ph | Me | H | H | H | Me | H | Me | 0 |
| 49 | 3-Br—Ph | Me | H | H | H | Me | H | Me | 0 |
| 50 | 4-Br—Ph | Me | H | H | H | Me | H | Me | 0 |
| 51 | 4-CN—Ph | Me | H | H | H | Me | H | Me | 0 |
| 52 | 3-PhO—Ph | Me | H | H | H | Me | H | Me | 0 |
| 53 | 4-PhO—Ph | Me | H | H | H | Me | H | Me | 0 |
| 54 | 4-BnO—Ph | Me | H | H | H | Me | H | Me | 0 |
| 55 | 2,3-F$_2$—Ph | Me | H | H | H | Me | H | Me | 0 |
| 56 | 2,4-F$_2$—Ph | Me | H | H | H | Me | H | Me | 0 |
| 57 | 2,5-F$_2$—Ph | Me | H | H | H | Me | H | Me | 0 |
| 58 | 2,6-F$_2$—Ph | Me | H | H | H | Me | H | Me | 0 |
| 59 | 3,4-F$_2$—Ph | Me | H | H | H | Me | H | Me | 0 |
| 60 | 3,5-F$_2$—Ph | Me | H | H | H | Me | H | Me | 0 |
| 61 | 4-OH—Ph | Me | H | H | H | Me | H | Me | 0 |
| 62 | 4-AcO—Ph | Me | H | H | H | Me | H | Me | 0 |
| 63 | (Me)$_2$N(CO)O—Ph | Me | H | H | H | Me | H | Me | 0 |
| 64 | (Me)$_2$NSO$_2$—O—Ph | Me | H | H | H | Me | H | Me | 0 |
| 65 | 4-CF$_2$HO—Ph | Me | H | H | H | Me | H | Me | 0 |
| 66 | 4-CF$_3$O—Ph | Me | H | H | H | Me | H | Me | 0 |
| 67 | 4-FCH$_2$CF$_2$O—Ph | Me | H | H | H | Me | H | Me | 0 |
| 68 | 4-SMe—Ph | Me | H | H | H | Me | H | Me | 0 |
| 69 | 4-SO$_2$Me—Ph | Me | H | H | H | Me | H | Me | 0 |
| 70 | 4-SCF$_3$—Ph | Me | H | H | H | Me | H | Me | 0 |
| 71 | 3,4-(Me)$_2$—Ph | Me | H | H | H | Me | H | Me | 0 |
| 72 | 2,3-(OMe)$_2$—Ph | Me | H | H | H | Me | H | Me | 0 |
| 73 | 2,5-(Cl)$_2$—Ph | Me | H | H | H | Me | H | Me | 0 |
| 74 | 3-F,4-Me—Ph | Me | H | H | H | Me | H | Me | 0 |
| 75 | 4-F,3-Me—Ph | Me | H | H | H | Me | H | Me | 0 |
| 76 | 3-F,4-OMe—Ph | Me | H | H | H | Me | H | Me | 0 |
| 77 | 4-F,3-OMe—Ph | Me | H | H | H | Me | H | Me | 0 |
| 78 | 2-Cl,4-OMe—Ph | Me | H | H | H | Me | H | Me | 0 |
| 79 | 3-Cl,4-OMe—Ph | Me | H | H | H | Me | H | Me | 0 |
| 80 | 3-F,4-Cl—Ph | Me | H | H | H | Me | H | Me | 0 |
| 81 | 2-F,4-Cl—Ph | Me | H | H | H | Me | H | Me | 0 |
| 82 | 4-F,2-Cl—Ph | Me | H | H | H | Me | H | Me | 0 |
| 83 | 4-F,3-Br—Ph | Me | H | H | H | Me | H | Me | 0 |
| 84 | 2-F,3-CF$_3$—Ph | Me | H | H | H | Me | H | Me | 0 |
| 85 | 2-F,4-CF$_3$—Ph | Me | H | H | H | Me | H | Me | 0 |
| 86 | 2-F,5-CF$_3$—Ph | Me | H | H | H | Me | H | Me | 0 |
| 87 | 3-F,4-CF$_3$—Ph | Me | H | H | H | Me | H | Me | 0 |

TABLE 1-continued

| No. | A | D | E | R1 | R2 | R3 | R4 | R5 | n |
|---|---|---|---|---|---|---|---|---|---|
| 88 | 3-F,5-$CF_3$—Ph | Me | H | H | H | Me | H | Me | 0 |
| 89 | 4-F,2-$CF_3$—Ph | Me | H | H | H | Me | H | Me | 0 |
| 90 | 4-F,3-$CF_3$—Ph | Me | H | H | H | Me | H | Me | 0 |
| 91 | 2-$CHF_2$O,4-OMe—Ph | Me | H | H | H | Me | H | Me | 0 |
| 92 | 3,5-F2,4-OMe—Ph | Me | H | H | H | Me | H | Me | 0 |
| 93 | Ph | Me | H | H | H | Me | Me | Me | 0 |
| 94 | Ph | Me | H | H | H | Me | Et | Et | 0 |
| 95 | Ph | $CO_2Et$ | H | H | H | Me | H | Me | 0 |
| 96 | Ph | $SO_2Me$ | H | H | H | Me | H | Me | 0 |
| 97 | Ph | OMe | H | H | H | Me | H | Me | 0 |
| 98 | Ph | Et | H | H | H | Me | H | Me | 0 |
| 99 | Ph | Ph | H | H | H | Me | H | Me | 0 |
| 100 | Ph | $CF_3$ | H | H | H | Me | H | Me | 0 |
| 101 | Ph | H | Ph | H | H | Me | H | Me | 0 |
| 102 | 4-F—Ph | Me | H | H | H | H | H | Me | 0 |
| 103 | Ph | Me | H | H | H | $FCH_2$ | H | Me | 0 |
| 104 | 4-F—Ph | Me | H | H | H | $FCH_3$ | H | Me | 0 |
| 105 | Ph | Me | H | H | H | 2-propenyl | H | Me | 0 |
| 106 | Ph | Me | H | H | H | Bn | H | Me | 0 |
| 107 | Ph | Me | H | H | H | 2-propynyl | H | Me | 0 |
| 108 | Me | Ph | H | H | H | Me | H | Me | 0 |
| 109 | Ph | Me | H | H | H | Me | H | Me | 1 |
| 110 | 4-J1—Ph | Me | H | H | H | Me | H | Me | 0 |
| 111 | 4-J2—Ph | Me | H | H | H | Me | H | Me | 0 |
| 112 | 4-J3—Ph | Me | H | H | H | Me | H | Me | 0 |
| 113 | Ph | Me | Me | H | H | Me | H | Me | 0 |
| 114 | Ph | Me | Me | Me | H | Me | H | Me | 0 |
| 115 | Ph | Me | Cl | H | H | Me | H | Me | 0 |
| 116 | Ph | Me | Br | H | H | Me | H | Me | 0 |
| 117 | Ph | Me | I | H | H | Me | H | Me | 0 |

In the formula (2): R6 = R7 = H:J1 R6 = H, R7 = Me:J2
In the formula (3): R8 = H, R9 = R10 = Me:J3

TABLE 1-2

| | | | | Cyclic amines | | |
|---|---|---|---|---|---|---|
| No | A | D | E | R1,R2 | R3 | R4–R5 | n |
| 118 | Ph | Me | H | H | Me | G1 | 0 |
| 119 | Ph | Me | H | H | Me | G2 | 0 |
| 120 | Ph | Me | H | H | Me | G3 | 0 |
| 121 | Ph | Me | H | H | Me | G4 | 0 |
| 122 | Ph | Me | H | H | Me | G5 | 0 |

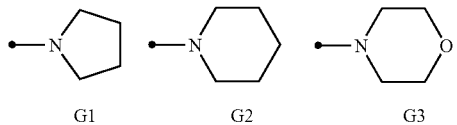

G1    G2    G3

G4    G5

TABLE 1-3

| No | A | D | E | R1 | R2 | R3 | R11 | R12 | n |
|---|---|---|---|---|---|---|---|---|---|
| 123 | Ph | Me | H | H | H | Me | H | $CO_2Me$ | 0 |
| 124 | Ph | Me | H | H | H | Me | Me | Me | 0 |

TABLE 2-1

δ value (ppm, solvent: CDCl3, internal reference: tetramethylsilane 1  2.03(3H, s), 2.89(3H, d), 4.01(3H, s), 5.17(2H, s), 6.62(1H, bs), 7.22(1H, s)
11  1.00–2.20(1H, m), 1.99(3H, s), 2.89(3H, d), 4.00(3H, s), 5.03(2H, s), 6.97(1H, bs), 7.18(1H, s)
13  2.89(3H, d), 4.02(3H, s), 5.27(2H, s), 6.49(1H, d), 7.24–7.82(5H, m)
14  2.87(3H, d), 4.01(3H, s), 5.20(2H, s), 6.70(1H, bs), 7.22–7.91(6H, m)
15  2.88(3H, d), 3.14(1H, s), 4.05(3H, s), 5.20(2H, s), 6.67(1H, bs), 7.07(2H, t), 7.73(1H, s), 8.03(2H, dd)
16  2.20(3H, s), 4.07(3H, s), 5.18(2H, s), 5.43(1H, bs), 6.67(2H, bs), 7.20–7.73(6H, m)
17  2.17(3H, s), 4.07(3H, s), 5.17(2H, s), 6.60(2H, bs), 7.25–7.64(5H, m)

TABLE 2-1-continued

δ value (ppm, solvent: CDCl3, internal reference: tetramethylsilane 18 2.21(3H, s), 2.84(3H, d,), 5.18(2H, s), 6.74(1H, bs), 7.24–7.66(6H, m)
19 1.15(3H, t), 2.19(3H, s), 3.35(2H, q), 4.06(3H, s), 5.17(2H, s), 6.72(1H, bs), 7.27–7.65(6H, m)
20 2.27(3H, s), 2.58(6H, s), 4.00(3H, s), 5.17(2H, s), 7.21–7.70(7H, m)
21 0.61–0.89(4H, m), 2.14(3H, s), 2.62–2.85(1H, m), 4.02(3H, s), 5.19(2H, s), 6.89(1H, s), 7.38–7.69(6H, m)
22 1.38(9H, s), 2.10(3H, s), 4.04(2H, s), 5.16(2H, s), 6.57(1H, bs), 7.25–7.65(6H, m)
23 1.21–2.06(8H, m), 2.18(3H, s), 3.86–4.29(1H, m), 4.02(3H, s), 5.17(2H, s), 6.65(1H, bs), 7.21–7.58(6H, m)
24 1.16–1.94(10H, m), 2.18(3H, s), 3.65–4.08(1H, m), 4.04(3H, s), 5.17(2H, s), 6.52(1H, bs), 7.25–7.67(6H, m)
25 0.84–2.03(13H, m), 2.20(3H, s), 4.02(3H, s), 5.20(2H, s), 6.49(1H, bs), 7.21–7.70(7H, m)
26 2.19(3H, s), 4.03(3H, s), 5.20(2H, s), 5.06–5.30(4H, m), 5.63–6.07(1H, m), 6.82(1H, m)7.22–7.70(6H, m)
27 2.19(3H, s), 2.21(1H, s), 4.08(3H, s), 4.17(2H, d), 5.18(2H, s), 6.99(1H, bs), 7.23–7.72(6H, m)
28 2.10(3H, s), 3.35–4.19(4H, m), 4.51(1H, t), 5.20(2H, s), 6.90(1H, bs), 7.25–7.70(7H, m)
29 2.28(3H, s), 4.21(3H, s), 4.51, 5.30(2H, s), 7.00–7.85(11H, m), 8.21(1H, bs)
30 2.20(3H, s), 4.00(3H, s), 4.50(2H, d), 5.21(2H, s), 6.95–7.70(12H, m)
31 1.50(3H, d), 2.19(3H, s), 4.01(3H, s), 5.19(2H, s), 7.01(1H, d), 7.34–7.71(12H, m)
32 2.18(3H, s), 2.69(2H, t), 3.53(2H, q), 3.82(6H, s), 4.00(3H, s)5.18(2H, s), 6.68–7.70(10H, m)
33 2.14(3H, s), 4.00(3H, s), 4.79(2H, s), 5.17(2H, s), 6.98(1H, bs), 7.25–7.70(5H, m)
34 2.19(3H, s), 3.78–4.14(2H, m), 4.09(3H, s), 5.20(2H, s), 7.07(1H, bs), 7.24–7.65(6H, m)
35 1.93(3H, s), 2.22(3H, s), 2.87(3H, d), 4.00(3H, s), 5.20(2H, s), 6.70(1H, bs), 7.10–7.25(4H, m), 7.37(1H, s)
36 2.18(3H, s), 2.37(3H, s), 2.87(3H, d), 4.03(3H, s), 5.20(2H, s), 6.75(1H, bs), 7.00–7.53(5H, m)
37 2.14(3H, s), 2.38(3H, s), 2.90(3H, d), 4.05(3H, s), 5.19(2H, s), 6.78(1H, bs), 7.14–7.78(5H, m)
38 1.28(6H, s), 2.00(1H, m), 2.00(3H, s), 2.90(3H, d), 4.01(3H, s), 5.19(2H, s), 6.56–7.80(6H, m)
39 2.21(3H, s), 2.86(3H, d), 4.02(3H, s), 5.20(2H, s), 6.48–7.92(11H, m)
40 2.22(3H, s), 2.88(3H, d), 4.04(3H, s), 5.21(2H, s), 6.70(1H, bs), 7.37(1H, s), 7.68(4H, q)
41 2.16(3H, s), 2.85(3H, d), 3.79(3H, s), 4.05(3H, s), 5.18(2H, s), 6.91(1H, bs), 6.85–7.62(5H, m)
42 2.04(3H, d), 2.84(3H, d), 4.00(3H, s), 5.19(2H, s), 6.75(1H, bs), 6.97–7.56(5H, m)
43 2.20(3H, s), 2.90(3H, d), 4.03(3H, s), 5.20(2H, s), 6.60–7.13(2H, m), 7.20–7.60(4H, m)
44 2.17(3H, s), 2.88(3H, d), 4.02(3H, s), 5.20(2H, s), 6.70(1H, bs), 6.90–7.70(5H, m)
45 1.98(3H, s), 2.85(3H, d), 4.00(3H, s), 5.20(2H, s), 6.41–7.80(6H, m)
46 2.20(3H, s), 2.88(3H, d), 4.02(3H, s), 5.19(2H, s), 6.37–8.20(6H, m)
47 2.17(3H, s), 4.03(3H, s), 5.18(2H, s), 6.75(1H, bs), 7.23–7.64(5H, m)
48 1.97(3H, s), 2.87(3H, d), 4.01(3H, s), 5.20(2H, s), 6.32–7.99(6H, m)
49 2.20(3H, s), 2.87(3H, d), 4.03(3H, s), 5.20(2H, s), 6.38–8.09(6H, m)
50 2.18(3H, s), 2.89(3H, d), 4.02(3H, s), 5.18(2H, s), 6.49–7.82(6H, m)
51 2.20(3H, s), 2.87(3H, d), 4.03(3H, s), 5.20(2H, s), 6.80(1H, bs), 7.40(1H, s), 7.60(2H, d), 7.80(2H, d)
52 2.13(3H, s), 2.85(3H, d), 4.00(3H, s), 5.17(2H, s), 6.72(1H, bs), 6.83–7.47(10H, m)
53 2.18(3H, s), 2.86(3H, d), 4.04(3H, s), 5.19(2H, s), 6.72(1H, bs), 6.95–7.70(10H, m)
54 2.18(3H, s), 2.85(3H, d), 4.00(3H, s), 5.08(2H, s), 5.18(2H, s), 6.56–7.31(1H, m)
55 1.98(3H, s), 2.85(3H, d), 4.00(3H, s), 5.21(2H, s), 6.68(1H, bs), 7.00–7.39(4H, m)
56 2.01(3H, s), 2.90(3H, d), 4.02(3H, s), 5.21(2H, s), 6.71–7.59(5H, m)
57 2.01(3H, d), 2.98(3H, d), 4.05(3H, s), 5.19(2H, s)6.70(1H, bs), 6.91–7.39(4H, m)
58 1.95(3H, s), 2.85(3H, d), 3.83(3H, s), 5.01(3H, s), 6.62(1H, bs), 6.92–7.55(5H, m)
59 2.10(3H, s), 2.90(3H, d), 4.03(3H, s), 5.19(2H, s), 6.67(1H, bs), 6.95–7.63(4H, m)
60 2.10(3H, s), 2.88(3H, d), 4.05(3H, s), 5.18(2H, s), 6.32–7.36(4H, m), 8.01(1H, bs)
61 2.13(3H, s), 2.90(3H, d), 4.01(3H, s), 5.19(2H, s), 6.40–7.62(6H, m)
62 2019(3H, s), 2.29(3H, s), 4.01(3H, s), 5.18(2H, s), 6.50–7.80(6H, m)
63 2.12(3H, s), 2.83(3H, d), 3.68(6H, s), 4.01(3H, s), 5.19(2H, s), 6.62–7.70(6H, m)
65 2.20(3H, s), 2.90(3H, d), 4.10(3H, s), 5.20(2H, s), 6.50(1H, t), 6.60–6.90(1H, m), 7.25(1H, s), 7.40(4H, q)
66 2.20(3H, s), 2.90(3H, d), 4.05(3H, s), 5.20(2H, s), 6.50–6.95(1H, m), 7.21(1H, s), 7.38(1H, s), 7.80(2H, s)
67 2.20(3H, s), 2.90(3H, d), 4.05(3H, s), 5.20(2H, s), 5.90(1H, t), 6.60–6.80(1H, m), 7.25(1H, s), 7.50(4H, m)
68 2.20(3H, s), 2.50(3H, s), 2.90(3H, d), 4.00(3H, s), 5.20(2H, s), 6.60–6.80(1H, m), 7.20(1H, s), 7.40(4H, q)
69 2.20(3H, s), 2.90(3H, d), 3.00(3H, s), 4.05(3H, s), 5.20(2H, s), 6.60–6.80(1H, m), 7.40(1H, s), 7.80–7.90(4H, bs)
70 2.18(3H, s), 2.85(3H, d), 4.03(3H, s), 5.18(2H, s), 6.70(1H, bs), 7.35–7.84(5H, m)
71 2.18(3H, s), 2.30(6H, s), 2.89(3H, d), 4.03(3H, s), 5.18(2H, s)6.53–7.57(6H, m)
72 2.02(3H, s), 2.90(3H, d), 3.59(3H, s), 3.90(3H, s), 5.22(2H, s), 6.73(1H, bs), 6.85–7.36(4H, m)
73 2.00(3H, s), 2.90(3H, d), 4.15(3H, s), 5.21(2H, s), 6.70(1H, bs), 7.18–7.41(4H, m)

TABLE 2-2

δ value (ppm, solvent: CDCl3, internal reference: tetramethylsilane 74 2.16(3H, s), 2.29(3H, s), 2.82(3H, d), 4.00(3H, s), 5.18(2H, s), 6.50–7.59(5H, m)
75 2.17(3H, s), 2.35(3H, d), 2.86(2H, d), 4.05(3H, s), 5.19(2H, s), 6.70(1H, bs), 6.84–7.51(4H, m)
76 2.10(3H, s), 2.90(3H, d), 3.90(3H, s), 4.00(3H, s), 5.20(2H, s), 6.60–6.80(1H, m), 7.25(1H, s), 7.20–7.50(3H, m)
77 2.20(3H, s), 2.82(3H, d), 3.90(3H, s), 4.00(3H, s), 5.20(2H, s), 6.60–6.80(1H, m), 7.00–7.25(3H, m), 7.30(1H, s)
78 2.10(3H, s), 2.86(3H, d), 3.90(3H, s), 4.00(3H, s), 5.20(2H, s), 6.60–7.00(2H, m), 7.25(1H, s), 7.40–7.90(2H, m)
79 1.90(3H, s), 2.80(3H, d), 3.80(3H, s), 4.00(3H, s), 5.20(2H, s), 6.60–7.00(2H, m), 7.18(1H, m), 7.20–7.40(2H, m)
80 2.20(3H, s), 2.88(3H, d), 4.04(3H, s), 5.19(2H, s), 6.66(1H, bs), 7.25–7.55(4H, m)
81 2.00–2.10(3H, m), 2.85(3H, d), 4.05(3H, s), 5.20(2H, s), 7.20(1H, s), 7.00–7.50(3H, m)
82 1.90(3H, s), 2.85(3H, d), 4.00(3H, s), 5.20(2H, s), 6.60–6.80(1H, m), 7.15(1H, s), 6.90–7.40(3H, m)
83 2.20(3H, s), 2.90(3H, d), 4.06(3H, s), 5.20(2H, s), 5.25(2H, s), 6.70(1H, bs), 7.00–7.88(4H, m)
84 2.04(3H, s), 2.89(3H, d), 4.02(3H, s), 5.20(2H, s), 6.41–7.89(5H, m)
85 2.01(3H, s), 2.90(3H, d), 4.01(3H, s), 5.22(2H, s), 6.44–7.98(5H, m)
86 2.23(3H, s), 2.90(3H, d), 4.01(3H, s), 5.21(2H, s), 6.37–8.10(5H, m)
87 2.21(3H, s), 2.90(3H, d), 4.05(3H, s), 5.20(2H, s), 6.40–8.01(5H, m)

TABLE 2-2-continued

δ value (ppm, solvent: CDCl3, internal reference: tetramethylsilane

| | |
|---|---|
| 88 | 2.20(3H, s), 2.88(3H, d), 4.00(3H, s), 5.20(2H, s), 6.37–8.23(5H, m) |
| 89 | 1.83(3H, s), 2.90(3H, d), 3.99(3H, s), 5.19(2H, s), 6.41–7.79(5H, m) |
| 90 | 2.43(3H, s), 3.20(3H, d), 4.52(3H, s), 5.75(2H, s), 7.40(1H, bs), 7.82–8.57(4H, m) |
| 91 | 2.20(3H, s), 2.85(3H, d), 3.85(3H, s), 4.08(3H, s), 5.20(2H, s), 6.60(1H, t), 7.00(1H, s), 7.22(1H, s)7.28–7.50(2H, m) |
| 92 | 2.17(3H, s), 2.87(3H, d), 4.00(3H, s), 4.05(3H, s), 5.17(2H, s), 6.70(1H, bs), 7.27(1H, s), 7.35(1H, s) |
| 93 | 2.19(3H, s), 2.64(3H, s), 2.81(3H, s), 3.99(3H, s), 5.20(2H, s), 6.90–7.65(5H, m) |
| 94 | 0.82(3H, t), 1.05(3H, t), 2.17(3H, s), 3.26(4H, q), 5.20(2H, s), 7.22–7.68(6H, m) |
| 95 | 1.27(3H, t), 2.90(3H, d), 4.05(3H, s), 4.21(2H, q), 6.67(1H, bs), 7.22–8.07(6H, m) |
| 96 | 2.80(3H, s), 2.87–2.84(3H, d), 4.10(3H, s), 5.25(2H, s), 6.64(1H, bs), 7.40–7.95(5H, m), 8.10(1H, s) |
| 97 | 2.97(3H, s), 3.80(3H, s), 3.83(3H, s), 5.16(2H, s), 6.65(1H, s), 7.20–8.00(5H, m) |
| 98 | 1.19(3H, d), 2.61(2H, q), 4.01(3H, s), 5.20(2H, s), 6.76(1H, bs), 7.21–7.68(6H, m) |
| 99 | 2.90(5H, d), 4.02(3H, s), 5.22(2H, s), 6.71(1H, bs), 7.10–7.70(11H, m) |
| 100 | 2.90(3H, d), 4.00(3H, s), 5.20(2H, s), 6.37–8.04(7H, m) |
| 101 | 2.82(3H, d), 3.89(3H, s), 5.19(2H, s), 6.71(1H, bs), 7.71–7.81(11H, m) |
| 102 | 2.24(3H, s), 2.83(3H, d), 3.12(1H, bs), 5.26(2H, s), 6.81–7.68(6H, m) |
| 103 | 2.22(3H, s), 2.91(3H, d), 5.24(2H, s), 5.75(2H, d), 6.70(1H, bs), 7.24–7.90(6H, m) |
| 104 | 2.18(3H, s), 2.90(3H, d), 5.24(2H, s), 5.75(2H, d), 6.70(1H, bs), 6.92–7.70(5H, m) |
| 105 | 2.18(3H, s), 2.83(3H, d), 2.67(2H, m), 5.16–5.38(2H, m), 5.19(2H, s), 6.82(1H, bs), 7.26–7.64(6H, m) |
| 106 | 2.18(3H, s), 2.83(3H, d), 5.23(2H, s), 5.25(2H, s), 6.66(1H, bs), 7.30–7.62(11H, m) |
| 107 | 2.17(3H, s), 2.51(1H, t), 2.85(3H, d), 4.78(2H, d), 5.21(2H, s), 6.80(1H, bs), 7.25–7.70(6H, m) |
| 108 | 2.41(3H, s), 2.84(3H, d), 4.05(3H, s), 5.16(2H, s), 6.77(1H, bs), 7.19–7.65(6H, m) |
| 109 | 2.08(3H, s), 2.10(3H, t), 2.89(3H, d), 3.99(3H, s), 4.02(2H, t), 7.18–7.96(6H, m) |
| 110 | 2.20(3H, s), 2.88(3H, d), 4.03(3H, s), 5.20(2H, s), 5.60(1H, bs), 7.37(1H, s), 7.47–7.80(4H, m), 8.13(1H, s) |
| 111 | 3H, s2.20(3H, s), 2.85(3H, d), 3.97(3H, s), 4.03(3H, s), 5.17(2H, s), 6.77(1H, bs), 7.35(1H, s), 7.40–7.80(4H, m), 8.05(1H, s) |
| 112 | 2.20(3H, s), 2.85(9H, m), 4.05(3H, s), 5.20(2H, s), 6.60–6.80(1H, m), 7.20(1H, s), 7.25(1H, s), 7.35–7.95(4H, m) |
| 118 | 1.62–1.99(4H, m), 2.10(3H, s), 3.10(2H, t), 3.37(2H, t), 3.99(3H, s), 5.21(2H, s), 7.22–7.68(6H, m) |
| 119 | 1.18–1.61(5H, m), 2.20(3H, s), 3.00–3.43(4H, m), 3.98(3H, s), 5.21(2H, s), 7.21–7.70(6H, m) |
| 120 | 2.21(3H, s), 3.18–3.78(4H, m), 3.97(3H, s), 5.21(2H, s), 7.22–7.68(6H, m) |
| 121 | 0.92(3H, d), 1.10(3H, d), 2.20(3H, s), 2.00–3.38(6H, m), 3.98(3H, s), 5.05(2H, s), 7.21–7.72(6H, m) |
| 122 | 2.18(3H, s), 2.35–2.55(4H, m), 3.70–3.80(4H, m), 3.94(3H, s), 5.20(2H, s), 7.25–7.67(6H, m) |
| 123 | 2.18(3H, s), 3.78(3H, s), 4.02(3H, s), 5.09(2H, s), 6.72(1H, bs), 7.22–7.77(6H, m), 8.48(1H, bs) |
| 124 | 2.27(3H, s), 2.58(6H, s), 4.00(3H, s), 5.17(2H, s), 7.21–7.70(7H, m) |

TABLE 3-1

| Compd. No. | Properties |
|---|---|
| 1 | m.p. 117–118° C. |
| 11 | m.p. 90–92° C. |
| 13 | Oily matter |
| 14 | m.p. 117–119° C. |
| 15 | m.p. 81–82° C. |
| 16 | m.p. 167–168° C. |
| 17 | m.p. >200° C. |
| 18 | m.p. 139–140° C. |
| 19 | Oily matter |
| 20 | m.p. 81–82° C. |
| 21 | m.p. 95–96° C. |
| 22 | Oily matter |
| 23 | m.p. >200° C. |
| 24 | Resinous substance |
| 25 | Resinous substance |
| 26 | Oily matter |
| 27 | m.p. 40–41° C. |
| 28 | Oily matter |
| 29 | m.p. 170–171° C. |
| 30 | m.p. 93–94° C. |
| 31 | Resinous substance |
| 32 | Oily matter |
| 33 | m.p. 85–86° C. |
| 34 | m.p. 102–103° C. |
| 35 | m.p. 128–129° C. |
| 36 | Resinous substance |
| 37 | m.p. 99–100° C. |
| 38 | m.p. 100–101° C. |
| 39 | m.p. 124–125° C. |
| 40 | m.p. 128–129° C. |
| 41 | m.p. 99–100° C. |
| 42 | m.p. 102–103° C. |
| 43 | m.p. 118–119° C. |
| 44 | m.p. 84–85° C. |
| 45 | m.p. 108–111° C. |
| 46 | m.p. 76–78° C. |
| 47 | m.p. 119–121° C. |
| 48 | Oily matter |
| 49 | m.p. 94–96° C. |
| 50 | m.p. 110–112° C. |
| 51 | m.p. 133–134° C. |
| 52 | Resinous substance |
| 53 | Oily matter |
| 54 | m.p. 122–123° C. |
| 55 | m.p. 115–116° C. |
| 56 | m.p. 113–114° C. |
| 57 | m.p. 133–134° C. |
| 58 | m.p. 131–132° C. |
| 59 | m.p. 77–78° C. |
| 60 | m.p. 108–110° C. |
| 61 | m.p. 161–162° C. |
| 62 | m.p. 115–116° C. |
| 63 | m.p. 156–157° C. |
| 65 | m.p. 140–141° C. |

TABLE 3-2

| Compd. No. | Properties |
|---|---|
| 66 | m.p. 91–92° C. |
| 67 | m.p. 108–109° C. |
| 68 | m.p. 136–137° C. |
| 69 | m.p. 118–119° C. |
| 70 | m.p. 103–104° C. |
| 71 | m.p. 140–141° C. |
| 72 | m.p. 134–135° C. |
| 73 | m.p. 139–140° C. |
| 74 | m.p. 93–94° C. |

TABLE 3-2-continued

| Compd. No. | Properties |
|---|---|
| 75 | m.p. 86–87° C. |
| 76 | m.p. 96–97° C. |
| 77 | m.p. 99–100° C. |
| 78 | m.p. 117–118° C. |
| 79 | m.p. 112–113° C. |
| 80 | m.p. 135–136° C. |
| 81 | m.p. 81–82° C. |
| 82 | m.p. 115–116° C. |
| 83 | m.p. 94–95° C. |
| 84 | m.p. 117–119° C. |
| 85 | m.p. 101–103° C. |
| 86 | m.p. 119–121° C. |
| 87 | m.p. 108–109° C. |
| 88 | m.p. 110–111° C. |
| 89 | m.p. 140–142° C. |
| 90 | m.p. 121–122° C. |
| 91 | m.p. 109–110° C. |
| 92 | m.p. 117–118° C. |
| 93 | Oily matter |
| 94 | Oily matter |
| 95 | m.p. 118–119° C. |
| 96 | m.p. 111–112° C. |
| 97 | m.p. 182–183° C. |
| 98 | m.p. 49–50° C. |
| 99 | m.p. 112–113° C. |
| 100 | m.p. 103–104° C. |
| 101 | Resinous substance |
| 102 | m.p. 151–152° C. |
| 103 | m.p. 98–99° C. |
| 104 | Resinous substance |
| 105 | Resinous substance |
| 106 | Oily matter |
| 107 | Resinous substance |
| 108 | m.p. 154–155° C. |
| 109 | Oily matter |
| 110 | Oily matter |
| 111 | Resinous substance |
| 112 | m.p. 64–65° C. |
| 118 | Oily matter |
| 119 | Oily matter |
| 120 | Oily matter |
| 121 | Oily matter |
| 122 | Oily matter |
| 123 | m.p. 166–167° C. |
| 124 | Oily matter |

Formulations

Formulation Example 1

Production of Wettable Powder

10 Parts of each compound shown in Table 1 (Compounds Nos. 11 to 124), 83 parts of clay, 2 parts of white carbon, 2 parts of ligninsulfonic acid soda and 3 parts of alkylnaphthalenesulfonic acid soda were mixed and pulverized to give wettable powder.

Formulation Example 2

Production of Granules 2.5 Parts of each compound shown in Table 1 (Compounds Nos. 11 to 124), 28 parts of bentonite, 52 parts of talc, 2 parts of dodecylbenzenesulfonic acid soda and 2 parts of lignin sulfonic acid soda were mixed. To the mixture, 13.5 parts of water was added. The resulting mixture was kneaded by a kneader, granulated by a granulator and then subjected to drying and sieving to give granules.

Formulation Example 3

Production of Flowable

5 Parts of each compound shown in Table 1 (Compounds Nos. 11 to 124), 11 parts of propylene glycol, 3 parts of SORPOL 7290P (trade name, available from TOHO Chemical Industry Co., Ltd.), 0.1 part of TOXANONE N100 (trade name, available from Sanyo Chemical Industries, Ltd.), 0.2 part of ANTIFOAM E-20 (trade name, available from KAO Corporation), 1.5 parts of KUNIPIA F (trade name, available from Kunimine Industries Co, Ltd.) and 79.2 parts of water were well mixed. The mixture was wet pulverized to particle sizes of 5 μm or less. A flowable was thus obtained.

Formulation Example 4

Production of Emulsifiable Concentrate

5 Parts of each compound shown in Table 1 (Compounds Nos. 11 to 124) was dissolved in 50.5 parts of N-methylpyrrolidone. The solution was combined with 24.5 parts of SAS 296 (trade name, available from NIPPON PETROCHEMICALS COMPANY, LTD) and 20 parts of SORPOL 3880L (trade name, available from TOHO Chemical Industry Co., Ltd.). These were stirred to give a uniform solution. An emulsifiable concentrate was thus obtained.

Test of Herbicidal Effects

Examples of testing the herbicidal activity of the herbicide compositions of the invention are given below, but it should be construed that the invention is in no way limited to those test examples.

Test Example 1

Upland Field Foliage Treatment

A plastic pot of 130 cm$^2$ was filled with upland soil. Subsequently, weed seeds of *Setaria viridis, Digitaria adscendens, Chenopodium album* and *Stellaria media*, and crop seeds of soybean (*Glycine max*) and wheat (*Triticum aestivum*), were sowed and covered with soil of about 1 cm thickness. On the 14th day after the sowing, the wettable powder prepared in Formulation Example 1 was diluted with water such that the amount of the active ingredient became 1 kg per hectare, and then uniformly applied to the plant leaf surfaces. On the 21st day after the application, observation and evaluation were carried out according to the criteria described below.

The results are set forth in Table 4.

Test Example 2

Upland Soil Treatment

A plastic pot of 130 cm$^2$ was filled with upland soil. Subsequently, weed seeds of *Setaria viridis, Digitaria adscendens, Chenopodium album* and *Stellaria media*, and crop seeds of soybean (*Glycine max*) and wheat (*Triticum aestivum*), were sowed and covered with soil of about 1 cm thickness. On the next day after the sowing, the wettable powder prepared in Formulation Example 1 was diluted with water such that the amount of the active ingredient became 1 kg per hectare, and then uniformly applied to the soil surface. On the 21st day after the application, observation and evaluation were carried out according to the aforesaid criteria.

The results are set forth in Table 5.

Test Example 3

Paddy Field Treatment

A plastic pot of 130 cm$^2$ was filled with paddy soil, and soil puddling was carried out to adjust the submerged depth to 4 cm. Subsequently, seeds of *Echinochloa crusgalli*, *Monochoria vaginalis, Ammannia multiflora* and *Scirpus juncoides* were sowed, and rice (*Oryza sative*, variety: *Koshihikari*) of two-leaf period was transplanted by 2 rice plants of 1 stub per pot at a depth of 3 cm. On the 10th day after the transplantation, the wettable powder prepared in Formulation Example 1 was diluted with water such that the amount of the active ingredient became 1 kg per hectare, and then dropped to diffuse on the water surface. On the 21st day after the dropping, observation and evaluation were carried out according to the aforesaid criteria.

The results are set forth in Table 6.

<Evaluation Criteria>

Herbicidal activity was evaluated based on the following criteria.

Index: 0–5

5: herbicidal effect of not less than 90%, or phytotoxicity of 90% or more

4: herbicidal effect of not less than 70% and less than 90%, or phytotoxicity of 70% or more and less than 90%

3: herbicidal effect of not less than 50% and less than 70%, or phytotoxicity of 50% or more and less than 70%

2: herbicidal effect of not less than 30% and less than 50%, or phytotoxicity of 30% or more and less than 50%

1: herbicidal effect of not less than 10% and less than 30%, or phytotoxicity of 10% or more and less than 30%

0: herbicidal effect of not less than 0% and less than 10%, or phytotoxicity of 0% or more and less than 10%

TABLE 4-1

| Compd. No. | Herbicidal activity | | | | | |
|---|---|---|---|---|---|---|
| | SV | DA | CA | SM | GM | TA |
| 11 | 3 | 5 | 5 | 3 | 0 | 0 |
| 13 | 3 | 4 | 4 | 4 | 0 | 0 |
| 14 | 5 | 5 | 5 | 5 | 0 | 0 |
| 17 | 5 | 5 | 5 | 5 | 0 | 0 |
| 18 | 5 | 5 | 5 | 5 | 0 | 0 |
| 19 | 5 | 5 | 5 | 5 | 0 | 0 |
| 20 | 2 | 3 | 5 | 5 | 0 | 0 |
| 21 | 5 | 5 | 5 | 5 | 0 | 0 |
| 23 | 3 | 3 | 4 | 4 | 0 | 0 |
| 24 | 4 | 3 | 4 | 4 | 0 | 0 |
| 26 | 4 | 5 | 5 | 5 | 0 | 0 |
| 27 | 5 | 5 | 5 | 5 | 0 | 0 |
| 28 | 3 | 3 | 4 | 3 | 0 | 0 |
| 30 | 3 | 4 | 4 | 3 | 0 | 0 |
| 33 | 4 | 5 | 4 | 4 | 0 | 0 |
| 34 | 4 | 5 | 4 | 4 | 0 | 0 |
| 36 | 4 | 5 | 5 | 4 | 0 | 0 |
| 37 | 5 | 5 | 5 | 5 | 0 | 0 |
| 41 | 5 | 5 | 5 | 5 | 1 | 0 |
| 42 | 5 | 5 | 5 | 5 | 0 | 0 |
| 43 | 5 | 5 | 5 | 5 | 0 | 0 |
| 44 | 5 | 5 | 5 | 5 | 0 | 0 |
| 46 | 5 | 5 | 5 | 5 | 0 | 0 |
| 47 | 5 | 5 | 5 | 5 | 0 | 0 |
| 53 | 4 | 5 | 5 | 4 | 0 | 0 |

TABLE 4-1-continued

| Compd. No. | Herbicidal activity | | | | | |
|---|---|---|---|---|---|---|
| | SV | DA | CA | SM | GM | TA |
| 54 | 4 | 5 | 4 | 4 | 0 | 0 |
| 56 | 5 | 5 | 5 | 5 | 0 | 0 |

SV: *Setaria viridis*
DA: *Digitaria adscendens*
CA: *Chenopodium album*
SM: *Stellaria media*
GM: Soybean (*Glycine max*)
TA: Wheat (*Triticum aestivum*)

TABLE 4-2

| Compd. No. | Herbicidal activity | | | | | |
|---|---|---|---|---|---|---|
| | SV | DA | CA | SM | GM | TA |
| 57 | 5 | 5 | 5 | 5 | 0 | 0 |
| 59 | 5 | 5 | 5 | 5 | 0 | 0 |
| 65 | 5 | 5 | 5 | 5 | 0 | 0 |
| 67 | 4 | 5 | 5 | 4 | 0 | 0 |
| 70 | 4 | 5 | 5 | 4 | 0 | 0 |
| 74 | 5 | 5 | 5 | 5 | 0 | 0 |
| 75 | 5 | 5 | 5 | 5 | 0 | 0 |
| 77 | 3 | 5 | 5 | 3 | 0 | 0 |
| 81 | 5 | 5 | 5 | 5 | 0 | 0 |
| 82 | 3 | 5 | 4 | 4 | 0 | 0 |
| 83 | 3 | 5 | 4 | 4 | 0 | 0 |
| 85 | 4 | 4 | 5 | 5 | 0 | 0 |
| 86 | 3 | 5 | 4 | 4 | 0 | 0 |
| 88 | 4 | 5 | 5 | 5 | 0 | 0 |
| 92 | 5 | 5 | 5 | 5 | 0 | 0 |
| 94 | 3 | 3 | 5 | 5 | 0 | 0 |
| 98 | 3 | 4 | 4 | 4 | 0 | 0 |
| 103 | 3 | 4 | 5 | 5 | 0 | 0 |
| 104 | 3 | 4 | 5 | 5 | 0 | 0 |
| 105 | 5 | 5 | 5 | 5 | 0 | 0 |
| 106 | 3 | 3 | 3 | 3 | 0 | 0 |
| 111 | 4 | 5 | 5 | 5 | 0 | 0 |
| 118 | 3 | 4 | 4 | 5 | 0 | 0 |
| 120 | 4 | 4 | 5 | 4 | 0 | 0 |
| 122 | 4 | 4 | 4 | 4 | 0 | 0 |
| 124 | 3 | 3 | 4 | 4 | 0 | 0 |

TABLE 5-1

| Compd. No. | Herbicidal activity | | | | | |
|---|---|---|---|---|---|---|
| | SV | DA | CA | SM | GM | TA |
| 13 | 4 | 4 | 5 | 5 | 0 | 0 |
| 14 | 5 | 5 | 5 | 5 | 1 | 0 |
| 17 | 4 | 4 | 4 | 4 | 0 | 0 |
| 18 | 5 | 5 | 5 | 5 | 0 | 0 |
| 19 | 5 | 5 | 5 | 5 | 0 | 0 |
| 20 | 3 | 4 | 3 | 4 | 0 | 0 |
| 21 | 4 | 4 | 5 | 5 | 0 | 0 |
| 23 | 4 | 4 | 5 | 4 | 0 | 0 |
| 24 | 4 | 3 | 5 | 4 | 0 | 0 |
| 26 | 4 | 5 | 5 | 5 | 0 | 0 |
| 27 | 5 | 5 | 5 | 5 | 1 | 0 |
| 28 | 3 | 4 | 4 | 3 | 0 | 0 |
| 30 | 4 | 3 | 4 | 3 | 0 | 0 |
| 33 | 4 | 5 | 5 | 5 | 0 | 0 |
| 34 | 4 | 5 | 5 | 5 | 0 | 0 |
| 36 | 4 | 4 | 5 | 5 | 1 | 0 |
| 37 | 5 | 5 | 5 | 5 | 0 | 0 |
| 41 | 5 | 5 | 5 | 5 | 1 | 0 |
| 43 | 5 | 5 | 5 | 5 | 1 | 0 |
| 44 | 5 | 5 | 5 | 5 | 0 | 0 |
| 46 | 5 | 5 | 5 | 5 | 1 | 0 |
| 47 | 5 | 5 | 5 | 5 | 0 | 0 |

TABLE 5-1-continued

| Compd. No. | Herbicidal activity | | | | | |
|---|---|---|---|---|---|---|
| | SV | DA | CA | SM | GM | TA |
| 51 | 4 | 4 | 4 | 4 | 0 | 0 |
| 53 | 3 | 5 | 4 | 4 | 0 | 0 |
| 54 | 3 | 4 | 5 | 5 | 0 | 0 |
| 55 | 5 | 5 | 5 | 5 | 0 | 0 |

SV: *Setaria viridis*
DA: *Digitaria adscendens*
CA: *Chenopodium album*
SM: *Stellaria media*
GM: Soybean (*Glycine max*)
TA: Wheat (*Triticum aestivum*)

TABLE 5-2

| Compd. No. | Herbicidal activity | | | | | |
|---|---|---|---|---|---|---|
| | SV | DA | CA | SM | GM | TA |
| 56 | 5 | 5 | 5 | 5 | 1 | 0 |
| 57 | 5 | 5 | 5 | 5 | 0 | 0 |
| 59 | 5 | 5 | 5 | 5 | 0 | 0 |
| 65 | 5 | 5 | 5 | 5 | 0 | 0 |
| 67 | 4 | 4 | 5 | 5 | 0 | 0 |
| 70 | 3 | 3 | 4 | 4 | 0 | 0 |
| 74 | 4 | 5 | 5 | 5 | 1 | 0 |
| 75 | 4 | 4 | 5 | 5 | 1 | 0 |
| 77 | 4 | 5 | 5 | 5 | 0 | 0 |
| 81 | 5 | 5 | 5 | 5 | 1 | 0 |
| 82 | 4 | 5 | 4 | 5 | 0 | 0 |
| 83 | 5 | 5 | 5 | 5 | 0 | 0 |
| 86 | 4 | 5 | 5 | 5 | 1 | 0 |
| 88 | 4 | 4 | 5 | 5 | 0 | 0 |
| 92 | 5 | 5 | 5 | 5 | 0 | 0 |
| 94 | 3 | 3 | 5 | 4 | 0 | 0 |
| 98 | 3 | 4 | 4 | 5 | 0 | 0 |
| 103 | 4 | 5 | 5 | 5 | 0 | 0 |
| 104 | 4 | 5 | 5 | 5 | 0 | 0 |
| 105 | 4 | 4 | 4 | 4 | 0 | 0 |
| 106 | 3 | 4 | 4 | 4 | 0 | 0 |
| 111 | 4 | 4 | 5 | 5 | 0 | 0 |
| 118 | 3 | 3 | 4 | 4 | 0 | 0 |
| 120 | 3 | 4 | 4 | 4 | 0 | 0 |
| 122 | 3 | 3 | 4 | 4 | 0 | 0 |
| 124 | 3 | 3 | 5 | 4 | 0 | 0 |

TABLE 6-1

| Compd. No. | Herbicidal activity | | | | |
|---|---|---|---|---|---|
| | EC | SJ | MV | AM | OS |
| 11 | 5 | 5 | 5 | 5 | 1 |
| 14 | 5 | 5 | 5 | 5 | 1 |
| 17 | 4 | 4 | 5 | 5 | 0 |
| 18 | 5 | 5 | 5 | 5 | 0 |
| 19 | 5 | 5 | 5 | 5 | 0 |
| 20 | 5 | 4 | 5 | 4 | 0 |
| 21 | 5 | 5 | 5 | 5 | 0 |
| 23 | 4 | 4 | 5 | 5 | 0 |
| 24 | 4 | 4 | 5 | 4 | 0 |
| 26 | 5 | 5 | 5 | 5 | 0 |
| 27 | 5 | 5 | 5 | 5 | 0 |
| 30 | 4 | 4 | 5 | 4 | 0 |
| 31 | 3 | 4 | 5 | 4 | 0 |
| 33 | 5 | 4 | 5 | 5 | 0 |
| 34 | 5 | 5 | 5 | 5 | 1 |
| 35 | 5 | 4 | 4 | 4 | 0 |
| 37 | 5 | 5 | 5 | 5 | 1 |
| 38 | 5 | 5 | 5 | 5 | 0 |
| 40 | 5 | 5 | 5 | 5 | 0 |
| 41 | 5 | 5 | 5 | 5 | 0 |

TABLE 6-1-continued

| Compd. No. | Herbicidal activity | | | | |
|---|---|---|---|---|---|
| | EC | SJ | MV | AM | OS |
| 42 | 5 | 5 | 5 | 5 | 0 |
| 43 | 5 | 5 | 5 | 5 | 1 |
| 44 | 5 | 5 | 5 | 5 | 1 |
| 47 | 5 | 5 | 5 | 5 | 0 |
| 49 | 5 | 5 | 5 | 5 | 1 |
| 53 | 5 | 5 | 5 | 5 | 0 |

EC: *Echinochloa crusgalli*
SJ: *Scirpus juncoides*
MV: *Monochoria vaginalis*
AM: *Ammannia multiflora*
OS: Rice (*Oryza sativa*)

TABLE 6-2

| Compd. No. | Herbicidal activity | | | | |
|---|---|---|---|---|---|
| | EC | SJ | MV | AM | OS |
| 55 | 5 | 5 | 5 | 5 | 0 |
| 56 | 5 | 5 | 5 | 5 | 0 |
| 57 | 5 | 5 | 5 | 5 | 0 |
| 58 | 5 | 5 | 5 | 5 | 1 |
| 59 | 5 | 5 | 5 | 5 | 0 |
| 60 | 5 | 5 | 5 | 5 | 0 |
| 65 | 5 | 5 | 5 | 5 | 0 |
| 67 | 5 | 5 | 5 | 4 | 0 |
| 73 | 5 | 4 | 5 | 4 | 0 |
| 76 | 5 | 5 | 5 | 5 | 0 |
| 77 | 5 | 5 | 5 | 5 | 0 |
| 81 | 5 | 5 | 5 | 5 | 0 |
| 86 | 5 | 4 | 5 | 5 | 0 |
| 87 | 5 | 5 | 5 | 5 | 0 |
| 90 | 5 | 4 | 5 | 5 | 0 |
| 91 | 5 | 4 | 5 | 5 | 0 |
| 92 | 5 | 5 | 5 | 5 | 0 |
| 98 | 5 | 4 | 5 | 4 | 0 |
| 103 | 5 | 5 | 5 | 5 | 0 |
| 105 | 4 | 4 | 5 | 5 | 0 |
| 111 | 5 | 5 | 5 | 5 | 0 |
| 118 | 3 | 4 | 4 | 4 | 0 |
| 119 | 3 | 3 | 4 | 4 | 0 |
| 120 | 3 | 3 | 4 | 4 | 0 |
| 122 | 4 | 3 | 4 | 4 | 0 |
| 123 | 3 | 3 | 4 | 4 | 0 |

As shown in Tables 4 to 6, the wettable powder herbicides containing the inventive compound of the formula (1) or (4) exerted excellent herbicidal effects on various upland field weeds or paddy field weeds. They caused substantially no phytotoxicity to wheat (*Triticum aestivum*), soybean (*Glycine max*) and rice (*Oryza sativa*), with herbicidal activity evaluated mostly with the index 0.

The substituted pyrazole compounds of the present invention are novel substances synthesized from a pyrazole derivative and a haloalkyleneoxime ester derivative. They possess excellent herbicidal activity.

Herbicide compositions containing the substituted pyrazole compounds as active ingredients have high herbicidal effects and wide herbicidal spectra, can work sufficiently in a small dose, and are harmless to crops. Therefore, the herbicides containing the compounds as active ingredients are useful in agriculture, horticulture and many other fields.

What is claimed is:

1. A substituted pyrazole derivative represented by the formula (1):

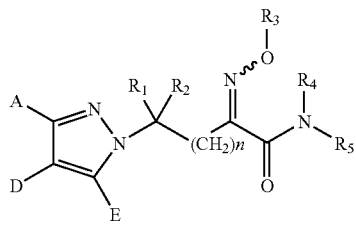

wherein:

n is 0 or 1; independently a group A is a hydrogen atom, a branched or unbranched alkyl group of 1 to 4 carbon atoms, a branched or unbranched haloalkyl group of 1 to 4 carbon atoms, a cycloalkyl group of 3 to 6 carbon atoms, or a phenyl group optionally having substituent groups;

said substituent groups being the same as or different from one another and selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, hydroxyl group, branched or unbranched haloalkoxy groups of 1 to 4 carbon atoms, branched or unbranched alkylcarbonyloxy groups of 1 to 4 carbon atoms, cycloalkylcarbonyloxy groups of 3 to 6 carbon atoms, branched or unbranched alkoxycarbonyloxy groups of 1 to 4 carbon atoms, branched or unbranched dialkylaminocarbonyloxy groups of 1 to 4 carbon atoms, branched or unbranched dialkylaminosulfonyloxy groups of 1 to 4 carbon atoms, branched or unbranched alkylthio groups of 1 to 4 carbon atoms, branched or unbranched haloalkylthio groups of 1 to 4 carbon atoms, branched or unbranched alkylsulfinyl groups of 1 to 4 carbon atoms, branched or unbranched haloalkylsulfinyl groups of 1 to 4 carbon atoms, branched or unbranched alkylsulfonyl groups of 1 to 4 carbon atoms, branched or unbranched haloalkylsulfonyl groups of 1 to 4 carbon atoms, halogen atoms, cyano group, nitro group, phenyl group optionally having substituent groups (the substituent groups are the same as the above substituent groups), phenoxy group optionally having substituent groups on the benzene ring (the substituent groups are the same as the above substituent groups) and benzyloxy group optionally having substituent groups on the benzene ring (the substituent groups are the same as the above substituent groups);

or said substituent groups being a group represented by the formula (2):

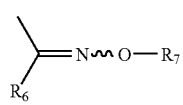

wherein $R_6$ and $R_7$ are the same or different and each denotes a hydrogen atom or a branched or unbranched alkyl group of 1 to 4 carbon atoms;

or said substituent groups being a group represented by the formula (3):

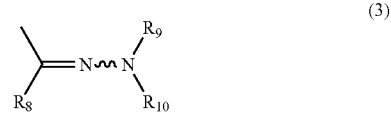

wherein $R_8$, $R_9$ and $R_{10}$ are the same or different and each denotes a hydrogen atom or a branched or unbranched alkyl group of 1 to 4 carbon atoms;

said substituent groups substituting a hydrogen atom at 0 to 5 arbitrary positions of the phenyl group;

a group D is a hydrogen atom, a branched or unbranched alkyl group of 1 to 4 carbon atoms, a branched or unbranched haloalkyl group of 1 to 4 carbon atoms, an alkenyl group of 2 to 4 carbon atoms, an alkynyl group of 2 to 4 carbon atoms, a branched or unbranched alkoxy group of 1 to 4 carbon atoms, a cycloalkyl group of 3 to 6 carbon atoms, a cyano group, a halogen atom, a branched or unbranched alkoxycarbonyl group of 1 to 4 carbon atoms, a branched or unbranched alkylthio group of 1 to 4 carbon atoms, a branched or unbranched alkylsulfinyl group of 1 to 4 carbon atoms, a branched or unbranched alkylsulfonyl group of 1 to 4 carbon atoms, or a phenyl group optionally having substituent groups (the substituent groups are the same as the aforesaid substituent groups), said substituent groups substituting a hydrogen atom at 0 to 5 arbitrary positions of the phenyl group;

a group E is a hydrogen atom, a branched or unbranched alkyl group of 1 to 4 carbon atoms, a cycloalkyl group of 3 to 6 carbon atoms, a halogen atom, or a phenyl group optionally having substituent groups (the substituent groups are the same as the aforesaid substituent groups), said substituent groups substituting a hydrogen atom at 0 to 5 arbitrary positions of the phenyl group;

groups $R_1$ and $R_2$ are the same or different and each denotes a hydrogen atom, a halogen atom, a branched or unbranched alkyl group of 1 to 4 carbon atoms, or a branched or unbranched haloalkyl group of 1 to 4 carbon atoms;

a group $R_3$ is a hydrogen atom, a branched or unbranched alkyl group of 1 to 4 carbon atoms, a branched or unbranched haloalkyl group of 1 to 4 carbon atoms, an alkenyl group of 2 to 4 carbon atoms, an alkynyl group of 2 to 4 carbon atoms, or a branched or unbranched alkoxyalkyl group of 1 to 4 carbon atoms;

groups $R_4$ and $R_5$ are the same or different and each denotes a hydrogen atom, a branched or unbranched alkyl group of 1 to 4 carbon atoms, a branched or unbranched haloalkyl group of 1 to 4 carbon atoms, a cycloalkyl group of 3 to 8 carbon atoms which may be substituted with a branched or unbranched alkyl group of 1 to 4 carbon atoms, an alkenyl group of 2 to 4 carbon atoms, an alkynyl group of 2 to 4 carbon atoms, a branched or unbranched alkoxyalkyl group of 1 to 4 carbon atoms, a cyanomethyl group, a substituted or unsubstituted amino group, or a phenyl group optionally having substituent groups;

said substituent groups being the same as or different from one another and selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group, wherein said substituent groups substitute a hydrogen atom at 0 to 5 arbitrary positions of the phenyl group;

or groups $R_4$ and $R_5$ are each a benzyl group optionally having substituent groups on the benzene ring;

said substituent groups being the same as or different from one another and selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group, wherein said substituent groups substitute a hydrogen atom at 0 to 5 arbitrary positions of the benzene ring;

or groups $R_4$ and $R_5$ are each an α- or β-phenethyl group optionally having substituent groups on the benzene ring, said substituent groups being selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group, wherein said substituent groups substitute a hydrogen atom at 0 to 5 arbitrary positions of the benzene ring;

or groups $R_4$ and $R_5$ together form a five-membered or six-membered aliphatic ring, wherein said ring may be substituted with a group selected from branched or unbranched alkyl groups of 1 to 4 carbon atoms, branched or unbranched haloalkyl groups of 1 to 4 carbon atoms, branched or unbranched alkoxy groups of 1 to 4 carbon atoms, branched or unbranched haloalkoxy groups of 1 to 4 carbon atoms, halogen atoms, cyano group and nitro group, and said ring may contain one or two heteroatoms.

2. A process for preparing substituted pyrazole derivatives of the formula (1), said process comprising reacting a pyrazole derivative of the formula (5) with a haloalkyleneoxime ester derivative of the formula (6) to obtain a pyrazole derivative ester of the formula (7):

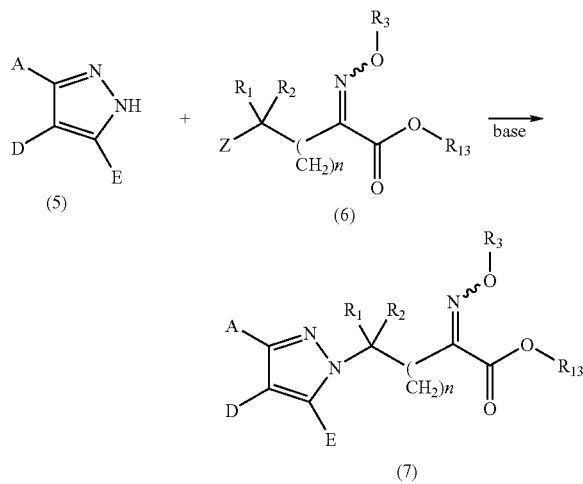

and hydrolyzing the ester group of the pyrazole derivative ester of the formula (7) in the presence of a base to yield a carboxylic acid derivative of the formula (8) and reacting the carboxylic acid derivative with an amine $R_4$—NH—$R_5$ in the presence of a condensation agent:

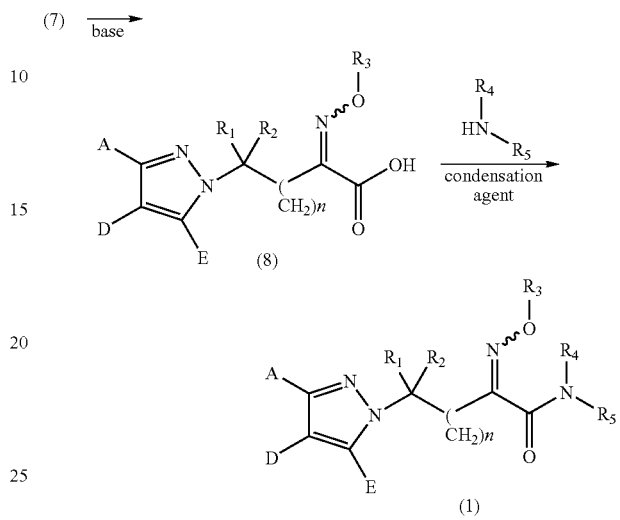

wherein in the formulae (5) to (8), n is 0 or 1, a group Z is a halogen atom, a group $R_{13}$ is a methyl or ethyl group, and each group A, D, E, $R_1$, $R_2$, $R_3$, $R_4$ and $R_5$ denotes independently the same substituent groups as in the formula (1).

3. A herbicide composition comprising one or more kinds of the substituted pyrazole derivatives of claim 1 as active ingredients.

4. A substituted pyrazole derivative represented by the following formula (1):

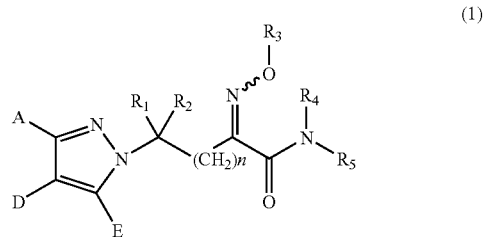

wherein:
n is 0 or 1; independently a group A is a hydrogen atom, a branched or unbranched alkyl group of 1 to 4 carbon atoms, a branched or unbranched haloalkyl group of 1 to 4 carbon atoms, a cycloalkyl group of 3 to 6 carbon atoms, or a phenyl group substituted with 0 to 5 substituent groups (0 substituent group means an unsubstituted phenyl group);

said substituent groups being the same as or different from one another and selected from alkyl groups of 1 to 4 carbon atoms, haloalkyl groups of 1 to 4 carbon atoms, alkoxy groups of 1 to 4 carbon atoms, haloalkoxy groups of 1 to 4 carbon atoms, alkylcarbonyloxy groups of 1 to 4 carbon atoms, alkoxycarbonyloxy groups of 1 to 4 carbon atoms, dialkylaminocarbonyloxy groups of 1 to 4 carbon atoms, alkylthio groups of 1 to 4 carbon atoms, haloalkylthio groups of 1 to 4 carbon atoms, alkylsulfinyl groups of 1 to 4 carbon atoms, haloalkylsulfinyl groups of 1 to 4 carbon atoms (these groups may be linear or branched), halogen atoms, hydroxyl group, cyano group, N-hydroxyimino group, N-methoxyimino group, N,N-dimethylaminoimino group, phenyl group, phenoxy group and benzyloxy group;

a group D is a hydrogen atom, a halogen atom, a branched or unbranched alkyl group of 1 to 4 carbon atoms, a branched or unbranched haloalkyl group of 1 to 4 carbon atoms, an alkynyl group of 2 to 4 carbon atoms, a branched or unbranched alkoxy group of 1 to 4 carbon atoms, an alkoxycarbonyl group of 1 to 4 carbon atoms, an alkylsulfinyl group of 1 to 4 carbon atoms or a phenyl group;

a group E is a hydrogen atom, a halogen atom, a branched or unbranched alkyl group of 1 to 4 carbon atoms or a phenyl group;

groups $R_1$ and $R_2$ are each a hydrogen atom or a methyl group;

a group $R_3$ is a hydrogen atom, a branched or unbranched alkyl group of 1 to 4 carbon atoms, an alkenyl group of 2 to 4 carbon atoms, an alkynyl group of 2 to 4 carbon atoms, a branched or unbranched alkoxyalkyl group of 1 to 4 carbon atoms, a fluoromethyl group or a benzyl group;

groups $R_4$ and $R_5$ together form a five-membered or six-membered aliphatic ring which may contain 1 or 2 heteroatoms and which may be substituted with an alkyl group of 1 to 4 carbon atoms, or independently a group $R_4$ is a hydrogen atom or a branched or unbranched alkyl group of 1 to 4 carbon atoms, and a group $R_5$ is a hydrogen atom, a branched or unbranched alkyl group of 1 to 4 carbon atoms, a branched or unbranched haloalkyl group of 1 to 4 carbon atoms, a branched or unbranched cyanoalkyl group of 1 to 4 carbon atoms, a cycloalkyl group of 3 to 6 carbon atoms which may be substituted with a branched or unbranched alkyl group of 1 to 4 carbon atoms, an alkenyl group of 2 to 4 carbon atoms, an alkynyl group of 2 to 4 carbon atoms, a phenyl group, a benzyl group, or an α- or β-phenethyl group optionally having a (branched or unbranched) alkoxy group of 1 to 4 carbon atoms on the benzene ring.

5. A herbicide composition comprising one or more kinds of the substituted pyrazole derivatives of claim 4 as active ingredients.

* * * * *